US007179901B2

(12) United States Patent
Sanicola-Nadel et al.

(10) Patent No.: US 7,179,901 B2
(45) Date of Patent: Feb. 20, 2007

(54) RENAL REGULATORY ELEMENTS AND METHODS OF USE THEREOF

(75) Inventors: Michele Sanicola-Nadel, Winchester, MA (US); Catherine Hession, Hingham, MA (US); Richard Tizard, Jr., Framingham, MA (US); Joseph Bonventre, Wayland, MA (US)

(73) Assignees: Biogen Idec MA Inc., Cambridge, MA (US); The General Hospital Corporation, Boston, MA (US)

( * ) Notice: Subject to any disclaimer, the term of this patent is extended or adjusted under 35 U.S.C. 154(b) by 381 days.

(21) Appl. No.: 10/311,388

(22) PCT Filed: Jun. 15, 2001

(86) PCT No.: PCT/US01/19295

§ 371 (c)(1),
(2), (4) Date: Mar. 28, 2003

(87) PCT Pub. No.: WO01/98481

PCT Pub. Date: Dec. 27, 2001

(65) Prior Publication Data

US 2003/0215831 A1    Nov. 20, 2003

Related U.S. Application Data

(60) Provisional application No. 60/212,131, filed on Jun. 16, 2000.

(51) Int. Cl.
*C07H 21/04*   (2006.01)
*C12N 15/63*   (2006.01)
*C12N 15/85*   (2006.01)
*C12N 15/00*   (2006.01)

(52) U.S. Cl. .................. 536/24.1; 435/320.1; 435/325; 435/69.1

(58) Field of Classification Search ...................... None
See application file for complete search history.

(56) References Cited

U.S. PATENT DOCUMENTS

| 5,622,861 | A  | 4/1997  | Kaplan et al.         |
| 6,664,385 | B1 | 12/2003 | Sanicola-Nadel et al. |
| 2003/0124114 | A1 | 7/2003 | McIntire et al.       |
| 2003/0215831 | A1 | 11/2003 | Sanicola-Nadel et al. |
| 2004/0005322 | A1 | 1/2004 | Kuchroo et al.        |
| 2004/0180038 | A1 | 9/2004 | Hancock et al.        |
| 2005/0095593 | A1 | 5/2005 | McIntire et al.       |
| 2005/0112117 | A1 | 5/2005 | Bailly et al.         |

FOREIGN PATENT DOCUMENTS

| WO | WO 96/04376  | 2/1996  |
| WO | WO 97/44459  | 11/1997 |
| WO | WO 97/44460  | 11/1997 |
| WO | WO 98/20110  | 5/1998  |
| WO | WO 01/98481  | 12/2001 |
| WO | WO 03/025138 | 3/2003  |
| WO | WO 03/042661 | 5/2003  |
| WO | WO 03/080856 | 10/2003 |
| WO | WO 04/005544 | 1/2004  |
| WO | WO 04/084823 | 10/2004 |
| WO | WO 05/001092 | 1/2005  |

OTHER PUBLICATIONS

Database No. AC005603, Homo sapiens subtelomeric cosmid 11b-1, Sep. 3, 1998.*
Adams et al. Use of a random human BAC end sequence database for sequence ready map building. Gene Bank accession No. AQ277590. Nov. 22, 1998.*
Bailly, V., et al., "Shedding of Kidney Injury Molecule-1, a Putative Adhesion Protein Involved in Renal Regeneration," Journal of Biological Chemistry, (2002) 277(42):39739-39748.
Berg et al., "L-selectin-mediated Lymphocyte Rolling on MadCAM-1," Nature (1993) 366:695-698.
Berlin et al., "alpha-4-beta-7 Integrin Mediates Lymphocyte Binding to the Mucosal Vascular Address in MAdCAM-1," Cell (1993) 74:185-195.
Bonventre and Colvin, "Adhesion Molecules in Renal Disease," Current Opinion in Nephrology and Hypertension (1996) 5:254-261.
Briskin et al., "MAdCAM-1 has Homology to Immunoglobulin and Mucin-like Adhesion Receptors and to IgA1," Nature (1993) 363:461-464.
Dudley et al., "A Requirement for Bone Morphogenetic Protein-7 During Development of the Mammalian Kidney and Eye," Genes & Development (1995) 9:2795-2807.
Fagotto and Gumbiner, "Cell Contact-Dependent Signaling," Developmental Biology (1996) 180:445-454.
Feigelstock et al., "The human homolog of HAVcr-1 codes for a hepatitis A virus cellular receptor," J. Virol. (1998) 72:6621-6628.
Greve et al., "The Major Hyman Rhinovirus Receptor Is ICAM-1," Cell (1989) 56:839-847.
Hubank and Schatz. "Identifying Differences in mRNA Expression by Representational Difference Analysis of cDNA," Nucleic Acids Research (1994) 22:5640-5648.
Kaplan et al. "Identification of a Surface Glycoprotein on African Green Monkey Kidney Cells as a Receptor for Hepatitis A Virus," EMBO (1996) 15:4282-96.
Klinken et al, "Mucin Gene Structure and Expression: Protection vs. Adhesion," Am J. Physiol. (1995) 269:G613-G627.
Kuchroo, et al. "The *Tim* Gene Family: Emerging Roles in Immunity and Disease," Nat. Rev. Immunol. (2003) 3:454-62.
Lin G. et al., "Expression of CD34 in endothelial cells, hematopoietic progenitors and nervous cells in fetal and adult mouse tissues, "Eur. J. Immunol. (1995) 25:1508-1516.
Luo et al., "BMP-7 is an Inducer of Nephrogensis and is also Required for Eye Development and Skeletal Patterning," Genes & Development (1995) 9:2808-2820.

(Continued)

*Primary Examiner*—Celine Qian
(74) *Attorney, Agent, or Firm*—Fish & Richardson P.C.

(57) ABSTRACT

Disclosed are cis-acting regulatory elements from a KIM-1 gene. The elements can be used to direct the expression of operably linked sequences in renal tissue.

14 Claims, 15 Drawing Sheets

OTHER PUBLICATIONS

McIntire et al. "Indentification of *Tapr* (An Airway Hyperreactivity Regulator Locus) and the Linked *Tim* Gene Family," Nat. Immunol. (2001):2:1109-16.

Monney et al., "Th1-Specific Cell Surfaces Protein Tim-3 Regulates Macrophage Activation and Severity of an Autoimmune Disease," Nature (2002) 415:536-41.

Muller et al., "Integrin alpha8-beta1 is Critically Important for Epithelial-Mesenchymal Interactions During Kidney Morphogenesis" Cell (1997) 88:603-613.

Owens et al., "The genetic engineering of monoclonal antibodies," J. Immunol. Methods. (1994) 168:149-165.

Rieger et al., Glossary of Genetics. 5th Edition, Springer-Verlag, NY, (1991) 16-17.

Rudikoff et al., "Single amino acid substitution altering antigen-bidning specificity," Proc. Nat. Acad. Sci., USA, (1982) 79:1979-1983.

Sastry and Horwitz, "Adhesion-Growth Factor Interactions During Differentiation: An Integrated Biological Response," Developmental Biology (1996) 180:455-467.

Shimizu et al., "Mucins in the Mainstream," Nature (1993) 336:630-631.

Shyjan et al., "Human Mucosal Addressin Cell Adhesion Molecule-1 (MAdCAM-1) Demonstrates Structural and Functional Similarities to the alpha-4-beta-7-Integrin Binding Domains of Murine MAdCAM-1," J. of Immunology (1996) 156:2851-2857.

Skolnick et al., "From genes to protein structure and function: novel applications of computational approaches in the genomic era," Tibtech (2000) 18:34-39.

Takada et al., "The Cytokine-adhesion Molecule Cascade in Ischemia/Reperfusion Injury of the Rat Kidney," J. Clin. Invest. (1997) 99:2682-2690.

Thadhani et al., "Acute Renal Failure," NEJM (1996) 334:1448-1460.

Thompson et al., "The Cys-Rich Region of Hepatitis A Virus Cellular Receptor 1 is Required for Binding of Hepatitis A Virus and Protective Monoclonal Antibody 190/4, "J. of Virology (1998) 72(5):3751-3761.

Weterman et al., "nmb, A Novel Gene, is Expressed in Low-Metastic Human Melanoma Cell Lines and Xenografts," Int. J. Cancer (1995) 60:73-81.

Database Accession No. AC026777 (XP-002207936), "Homo sapiens chromosome 5 clone CTC-332D4, complete sequence", retrieved from EMBL, Mar. 27, 2000.

Database Acession No. AQ277590 (XP-002207937), "CITBI-E1—2517G14.TF CITBI-E1 Homo sapiens genomic clone 2517G14, genomic survey sequence", retrieved from EMBL, Nov. 23, 1998.

Database Accession No. AL022721 (XP-002207938), "Human DNA Sequence from clone 109F14 on chromosome 6p21.2-21.3", retrieved from EMBL, Apr. 27, 1998.

Faure et al., "Differentially Expressed Genes in Ischemic Acute Renal Failure", Mol. Biol. of the Cell, Bethesda, MD, 1998, 9:473A (XP-000953127).

Ichimura et al., "Kidney Injury Molecule-1 (KIM-1), a Putative Epithelial Cell Adhesion Molecule . . . ", J. Biol. Chem. 273(7):4135-4142, 1998 (XP-002079926).

Padanilam et al., "Molecular mechanisms of cell death and regeneration in acute ischemic renal injury", Current Opinion in Nephrology and Hypertension, Rapid Science, London, GB, 1999, 8(1):15-19.

Rosenberg et al., "Differential gene expression in the recovery from ischemic renal injury", Kidney International 39:1156-1161, 1991 (XP-000953186).

\* cited by examiner

```
   1 GATCATACAA ACATGCTGTT ATTTTTATCA CTTAAAAAAA AAACACCCAG
  51 GATTTTCTCC TTCCATTTTT GCAAAACTTT TATTTTTTTT TTGGAAGATG
 101 GGGACTCACT CTGTCACTCA GGCTGGAATG CAGTAGTACT ACCATATCTC
 151 ACTGCAGCCT CAAACTCCTG GGCTCAAGTG ATCCTCCCG CTTAGCCTCC
 201 CAAATGGCTG GTACTATAGG CACTCAAGTC CAACTGCTTT TCTCCATGCA
 251 AACTCCTTGA AAGTGTTTCC TGTATTCAAT TATCTCCTGA TTTTCCTTCT
 301 TGTAAACTTT TTACTGCAGT ATAAAGTACT GGGGCTCACT GATAATCTCC
 351 AGCTTGCTCA GTCTATGACA AATCTTATTC CTTTCCTTTG CAGCATTTGA
 401 CTCATGATTG CTGCCTGTTC TTTGATGCGT TTGCTTCACT TGGCTTCTAG
 451 GACCTTTTTG CTTTTTCTCT TACCTCCTTG GCTGCTTCC ATTTCTGTAT
 501 TGGTGCCTCT TCCACCTCAG CATTTTTTTT TTTTTTTTT TTTAAGACGG
 551 AGTCTCGCTC TCTCGCCCAG GCTGGAGTGC AGTGGTGCGA TCTCGGCTCA
 601 CTGCAAGCTC CGCCTCCCAG GTTCACGCCA TTCTCCTGCC TCAGCCTCCT
 651 GAGTAGCTGG GACTATAGGC GCCCGCCACC ACGCCCGGCT AATTTCCACC
 701 TCAGCTTTAA CAAATTTTTT TAAAATTAAT TAATTTTTTT TTTTGAGACG
 751 GAGTCTTGCT CTGTCACTCA GCTGGAGTG CAGTGGCATG ATCTCGGCTC
 801 ACTGCGACCT CTGCCTCCCA GGTTCAAGCA ATTCTCCTGC CTCAGCCTCC
 851 TGAGTAGCTG GGATTACAGG CATGCGCCAT CACACCCGGC CAATTTTTGT
 901 GTTTTTAGTA GAGACGGGGT TTCACCATGT TGGCCAGGCT GGCCTGGAAC
 951 TCCTGACCTC AAGTGATCAG CCTGCCTTGG TCTCCTAAAG TGCTAAGACT
1001 GCAGGTGTGA GTCGCCACAC CCGGCCTTAA AATTTATTCT TATGTAGAGA
1051 TGGTGTTTCA CCATGTTGGC CAGGCTGACC TGGAACTCCT GACCTTAAGT
1101 TATCAGCCTG CCCCGGTCTC CCAAAGTGTT GGGATTACCT GCATGAGTCA
1151 ACATGCTTGT CCCCATTTTA ATCTTTTGAT GCTGGAAGGC CCCAGGACCT
```

Fig. 1A

```
1201 AGTCCTTAGC ATCAGGCATT CCTTTGAATC TCATCCTTTG AATTCCTACC

1251 TCATTCAGGC TCCTGGCTTT AAAATACCAT TTTTTTTTTT TTGAGGCGGA

1301 GTCTCGCTCT GTCGCGCAGT GGCGCGATCT CAGCTCACTG CAAGCTCCGC

1351 CTCCCAGGTT CACACCATTC TCCTGCCTCA GCCTCCCGAG TAGCTGGGAC

1401 TACAGGCACC TGCCACCACG CCTGGCTAAT TTTTTGTATT TTCAGTAGAG

1451 ACGGGGTTTC ATCGTGTTAC CCAGCACAGT CTCGATCTCG TGATCCGCCC

1501 ACCTCGGCCT CCCAAAGTGC TGGGATTACA GGCGTGAGCC ACCGCACCCA

1551 GCCAATACCA TTTCTAAGCC AGTAACTTGT AACTGTATCT TTAGCTCAGA

1601 CCTCCCTCCT GAACTCCAGC AGTCTCCACA CAGGTCTAAG ACATGTCAAA

1651 CTCAACATAC TTAAAACCCT GAATATTTCC TCTAAAACCT GTGGTCATGC

1701 AGGTTTTTGT TTTTTGTTTT TTGTTTTTTT TGAGATGGAG TCTTGCTCTG

1751 TTGCCCAGAC TAGAGTGCAG TGTCACGATC TTGGCTCACT CCAACCTCTG

1801 CCTCCTGGGT TCAAGCAATT CTCCTGGCTC AGCCTCCTGA GTAGCTCAGA

1851 TTACAGGCAC CCACGACCAT GCCTGGCTAA ATTTTTGTAT TTTTAGTAGA

1901 GACAGGGTTT TGCCATGTTG GCCAGGTTGG TCTTGAACTC CTGACCTCAG

1951 GTGATCCACC TGCCTTGGCC TCCCAAGGTG TTAGGATTAC AGGTGTGAGC

2001 CACTGAGCCC AGCCTTTGCA GCTCTCCTTG TCTTAATTGG CTGGAACCTC

2051 CAGCTCTTCC CGTGGCTCAG GCCGAAATCC TTGGAGTCAT CTTAGGCCCT

2101 TTCTCCTCAT ATCCTACAGG AAATCCTGTT TGCTCCACCT TCTCCACCTC

2151 CTTGGCTCAA GCCATTCTCC TGCCTCAGCC TCTTTAGTAG CTGGGACTAC

2201 AAGTTGCATG CCAGCATGCC TGGCTAATTT TTCTTTTTCT TTCTTTTTT

2251 TTTTTTTTG TAGAGACAGG GTCTCACTAT GTTGCCCTGA GCTCCTGGGC

2301 TCAAGCAGTC CTCCCGCCTT GGCCTCCCAA AGTCCAGGGA TTACAGCTGT
```

Fig. 1B

```
2351 GAGCCATCAC ATCTGGCTAC TCTAGGTTGA GTGAGGAAAG TTCATTGACC

2401 ACTTCCACTG CTAACCCATC TCTTCTGGAA TCTTTCCATA GTCTCCTGAC

2451 AGGTCTTCCT GCTTCTCAAT CTAGCAACCA CAGTGGTCCT TCTCAAAGGA

2501 AGTTAGATAC TGTCACCCTA TGCCCTTGCA GTGGTGCTTC TTTTCATGTG

2551 GGGTGAAAGC CTATGTCCTC AGAATATGGC TCCTAAGCCC CATGTGTCTG

2601 TCCTCTGCCC TCACTCCTCT GTGATCCCTG TCCCTCGCTC TGTTGCAGTC

2651 ACGCTGGCCT CTCTTGCCCT GTAAACACAC CAGGCACCCT CCTGCCTTAG

2701 GGCCTTTGCC CTTCTTGTCT GTCTCCATGG AAAGCGTTTG CTGTCTTGGC

2751 TAACTTCCTT GTCCTTTGTC TTAGTTCAAA TAATCACCTT CTTGGTGAAA

2801 GTAATAGAGA CTATTCAAAC CTGACCACCT TGTTTAAAAT TGCAACTCAG

2851 TGCCTCCTCA ACCCTCCACT CCCAACCACC TTCACCCTGC TCTTGTGTAT

2901 CCTTTTGCCT TTTTTGCATT AGCATTCCTC AACTTGTAAT ATGCTGATAA

2951 ATTACATTTT AGTGATGTTT TAAAAATCTG TATATTTATT TTTCAGTTAA

3001 AAGTTAGTTA CATGAGGCCA GGAGTGGTGC TCACGCCTAT AATCCCAGCA

3051 CTTTGGGAGG CCAAGGCGGG CAGATCACTT GAGGTCAGGA GTTCGTGACC

3101 AGCCTAACCA ACATGGTGAA ACCCCGTCTC TGCTAAAATT ACAAAAATTA

3151 GCCGGTGTGG TGATGCATGC CTGTAATCCC AGCTTCTTGG GAGGCTGAGG

3201 TAGGAGAATC GCTTGAACCC AGGAGGCAGA GTTTGCAGTG AGCTGAGATC

3251 GTGCCATTGC CCTCCAGCCT GGGCAAAAAA AGCGAAGCTC CATCTCAAAA

3301 AAAAAAAAAA AAATGTAAGT TACATGAGGC CAGGGGTCTT TGGTTCATTG

3351 GTACATTCCA GATGAATAGG ATCATTTCTA ACATATCGCA GATCATCAAC

3401 AAATAATTGT TAAATGAGTA CACTTTTGGT ATTTTTATAT ATTTTCTTTC

3451 TTTCTTTCTT TCTTTCTTTT TTTTTTGAG ACAGAATCTC GCTCTGTCAC

3501 CCAGGCTGGA GTGCAGTGGT GTGTGATCTC AGCTCACTGC AACCTCCACC
```

Fig. 1C

```
3551 TCCCAGGTTC AAGCGATTCT CTTGCCTCAG CCTCCCTAGT ATCTGAGACT

3601 ACAGGCACGC GCCACCACGC CTGGCTAATT TTTGTAGTTT TAGTAGAGAC

3651 AGGGGTTTGC CATATTGGCC AGGCTGGTCT TGAACTCCTA ACCTCAAGTG

3701 ATCCTCCTGC CTTGGCCTCC CAAAGTGCTG GGATTACAGG TGTGAGCCAC

3751 CATACTTGGG CTTTTATGTA TTTTCTATGG TAAACATAGG TGGTACCCTG

3801 TAATTTTTAT ATCTTTGTAA AAGATATAAA AAAAAGAAGC ATTATATTAC

3851 TTGTTATGAA ATCAGAGGAG TAAGTGAAGG AAAATAACTA GCTTAGGGCA

3901 GTGGGCAGGG CAGGAAGAGA ACTGAAAGGT AGGAAGACAG TTTTGGAGGG

3951 AATTGCAGAA GTCTGGATTA TAGAGGCCTA ATATAAAGTG ATGGGATGA

4001 GGGAGAGACT GACAGGTACA ATGATGTGGA GTTGGTGAGT CCCTAGTTGT

4051 GGAGGGGGCC TAAGAAGATC TTGCTGTGGT GAAAGCATGG GGAATATGAA

4101 CAGCTGAACT GTTTTGCAGG AGGCTGGAGC TGGAGGTACG ATGTGCGCTG

4151 AGATAGCAGG GAAGTAAGTG GTGATTGCAA GAAAGAACAG TGAATTATTT

4201 TCTTTTCTGA ATTCTTTCTT TTTTTTGAGA CAGGGTGTCA ATCTGTTGTC

4251 CAGGCTGGAG TGCAGTGGCA CGATCTCAGC TCACTGCAAC CTCCACCTCC

4301 CGGGTTCGAG CAATTCTCCT GCCTCAGCCT CCCAAGTAGC TGGGATTACA

4351 GGCACCCACC ACCGTGCCCG GCCCATGTTC TGAATCATTT CAATTCACTG

4401 CCGTTAATCT TGGTTTATAC AGATGCAGCT CCCTAGTGAG CAGCTGGAAA

4451 TTCAGCTTTG GTGCCCAAGT ATTGTCACTT CCAGCTTTAC CCTACAACTG

4501 GGATGCATCC TTCAGGGGGG TCATGAAGTT TGCCCTAAAG AGTAGTGATC

4551 CCTGGAGGTT GTATAGCTCA TTAAAAAAAT CCACTGTGCT ATATTGTTTG

4601 GGAGTCTTTA GAACACAGGC GTCTCTCATG GGAGATGGTC CTGTGTCAGA

4651 AAATTCAACC CTATGGAATT GTACAGTTAT GTAACATCTC AGAGCCTTGG
```

Fig. 1D

```
4701 CTCCACATCC CTGTCCTGGC TCTCTCTGGC TCATCATTTC CTCCAGTTGA
4751 AACACCCTCC ACCCATTCTT CTCACATGTC ACTTTTTAAG AAATTCTTCC
4801 CACCCCCCAC ATTCCGTCAT CAAAATGAAT GGTCTTTCCC TATGGGTTTG
4851 TGTTTCCATT TGTTTATCTA TTCAATTAAT AACTTTTTTT TTTTTGAGAA
4901 GTCTCACTCT GTGGCCCAGG CCAGAGTGCA GTGGCATGAT CTCCGCTCAG
4951 GGTAAATTCT GCCTCCCGGG TTCAGGCGAT TCTCTTGCCT CAGCCTCCTG
5001 AGTAGCTGGG ATTACAGGCA CCCGCCACCA CGCCTGGCTA ATTTTTGCAT
5051 TTTTGGTAGA GTTGGGTTTC ACCATGTTGG CCAGGCTGGT TTGGAACCCC
5101 TGACCTCAAG TGATCCTCCC ACCTCGGCCT CCTTTGGATT ACAGGTGTGA
5151 GCAACCATGC CTGGCTTCAA CACTTAAATT GCCTTAAAGG AGTTTATGGT
5201 CTGGAGTTGG GTGCCACACA ACACAGTCAC TATGTGTGAC AATTTAAATT
5251 TTATTTTTTT GTTTTTAATT AATTTATTTT TTTGAAAGCT CTGTCATCTA
5301 AGGCTTGAGT GCAGTGGTGC CATCTCAACT CCCCGAAGAC TGTCTCCTGG
5351 GCTCAAGCAA TCTGAAATTT TAATTAAAAT GAAATTAAAT AAAAATTTTT
5401 AGGCCAGGCA TGGCGGCTCA CACCTGTAAT TCCAGCACTT TTGGAAGTTG
5451 AGATGAGCGT ATCACTTGAG GCCAGGAGTT CCAGCCCAGC CTGGCCAACA
5501 TGGTGAAACT CCACCTCTGC TAAAAATACA AAAATTAGCC AGGCATGGTG
5551 GCGCGTGTCT GTAGTCCCAG CTACTCAGGA GACTGTGGCA AGAGAATCAC
5601 TTAAACCCAG GAGATGGAGG TTGCACTGAG CTGAGATTGT GACACTGCAC
5651 TCCAGCCTGG GTGACAGAGT CAGGCTCTGT CTTGGAAAAA AAAAAAATTA
5701 AAAATGCCTT GGTTGCCTTA GCCACATTTC AAGTGCTCAA TAGTCATATG
5751 TGGCTAGTGG CTGCTGTAGT GCACGACACT CACACAGAAT AACTCTGTAA
5801 CCAATATTCT ACTGGAGACA GAATCGATCC TATGGAATTC AAATTCAAAT
5851 CCTATGGAAT TGTACAGTTA TGTAACATCT CAGAGCACTG GCTCCACATC
```

Fig. 1E

```
5901 CCTGTCTTGG CTCTCTGTGG CTCATCAGTT CCAGAATAAC TCCGTTACCA
5951 GAATAACTCC ATTACTAAAA TTCTACCGGG CAGCACTCTA TAGGAGGGAA
6001 TAGAGACAGA CACCACATAT ATTGCACACA CAGATAAAAT GGATTAAGGA
6051 AAACAAGATA ATAATAGTGA GAGGGACTGG TTGGCTACTT TAGATTGAAG
6101 GACCTGTGAA AAATGTCCAG GGAGGTCATA TTTAAGCCGG GATAAAAATG
6151 AAAAGGAAAA AAGTGAAAAT GGTGGGGCTG GGGAGCTAGA TGGAGAACAC
6201 AGCCACGGAA AAGGCCTTAG GGTTGAGGCA AGTTGGAAAG AAAGCTCTAG
6251 TAGCTGGGGC TGAGTCAGCA GGGGAGAGAG TGGTAGAAGA AATCTATGGG
6301 GTAGGTCAGG GCCAGACCAC CAGGGCTTCA GTAATTTGAG TAAAGATTTA
6351 GGAATTATTA TTATTATTAT TATTATTATT TTTCTGAGAG AGTTATGAGA
6401 GGGTTATAAG TGGGGGAATG ATGTAGTCTG ATTATATATT TACCTTTACC
6451 TCACTTATCC TGATTTCATT AGTTGCTTAC TTACCCATGT CCCTGCCCGA
6501 TTGCACAAGT CTGGATTTTT GACGTCCCTA GTATATTGAG TCATGTCCCA
6551 TCAGCTCAAT ATGTTAGTAA TAACTGGTTG AATTGAATTA GCTTTTTTTT
6601 TTCAATCTTT TTTTCCTTAA GAAACAGGGT CTTGCTCTGT CACCCCGGCT
6651 GGTGTGCAGT GGCACAATCA TAGCCTCCAA CTGCTGGGCT CAAGCAACCC
6701 TCCTGCCTCA GCCTCCTGAG TAGCTGGGAC TACGGTCAGG TACACAAGGC
6751 CTGACTATAT TTTTTGTTCG TTTTTTTGCA GAGAGGGAGT CTTGCTATGT
6801 TGCCCAGGTT GGTCTCAAAC TCCTTACCTC AGGTGATCCA CTTGCCTTGG
6851 CCTCCCAAAG TGTTGGGATT ACAGGCGTGA GCCACTGTGC CTGGCAAGAA
6901 ATGAATTTTT ATTTTATTT TTGAGATGGA GTTTTGTTCT TGTTGTCCAG
6951 GCTAGAGTGC AATGGCTTGA TCTCGGCTCA CTGCAACCTC CACCTTCCAG
7001 GTTCAAGCAA TTCTTCTACC TCAGCCTCCT AAGTAGCTGG GATTACAGGC
```

Fig. 1F

```
7051 GCCCGCCACC ACCCCCAGCT AATTTTTGTA TTTTTAGTAG AGTCGGGGTT

7101 TCACCGTGTT AGCCAGGCTG GTCTTGAACT CCCGACCTCA GGTGACTGGC

7151 CTACTCGGCC TCCCAAAGTG CTGGGGTTAC AGGCACGAGC CACCATGCCC

7201 GGTCAAGAAA TGAATTTTTA AACGCTGCCA TACAAAACAC TATGCTGAGA

7251 TCATCCACTT CCCCATGAAC CCTGTCATGA GCTGCAAGAT ACAGACCACC

7301 ACTGCCTCCT TGGAAGTTAC TGAATTCTTA GACCAGAAGA GGAGTTAATG

7351 AAGTACTAGG CAAGCTTACT CATGTTTGTA TGGTTTAATG ATTAACAGCA

7401 GAAGTCAACA GCCCGATTTA ACGCATGTGG GTGCTTGACA CAGAGCCTGC

7451 TATATAGTAT TCTCCAAAAA CCTCAGCTAG TGCTATTACT GCATATGATG

7501 TAGGTTTAGT TTTCCAAGTT CTTCCGTGGC CCTTTTTGCT TATTATATCA

7551 ATCCTTGGTG GGAGATAGAG GAAGCATTTT TAGTGCTATT TTACAACTGA

7601 GGAAATAGAG GTTTGAAGAG AACTCAGGAA CTCTCAGGGT TACCCAGCAT

7651 TGTGAGTGAC AGAGCCTGGA TCTGAACGTA AGTCTGCTCC AGACTTCTGT

7701 TTCCTGAAGC ATTCTCTTGA AGTCCCTTGG TAAGGAGGTG TAGTCTGAAG

7751 CATGTTGTAC AGGAGCATGA AAGGTTAGGC ACAGTGATTC ACATTCACTC

7801 TCAATTTCTC TTGCTAATGG CAAACTTGGC AATATGACTG TTAAGGCTAG

7851 GGATAAGTCG TTGTGGCCAC TGAGTAGGAA AAGCTCCACG TCCACCAGAG

7901 GCCCAGTTTA CTCTGAAAAG CAAGTGCATC TCTGCCACTG GAAGGCTGGC

7951 ATTTGCTCTC GTGCTGCCAT TGAGCCACGC TGGTTCTCTG CTTCCAGTTT

8001 CCTTTTCTTT TCTTTTTTTT TGTTTTGTTT TTTGAGACGG AGTCTTGCTC

8051 TGTCGCCCAG GCTGGAGTGC AGTGGCGCGA TCTCGGCTCA CCGCAAGCTC

8101 CGCCTCCCGC GGGTTCACGC CATTCTCCTG CCTCAGCCTC CCGAGTAGCT

8151 GGGACTACAG GCGCCAGTGA CCACGCCCGG CTAATTTTTT GTATTTTTAG

8201 TAGAGACGGG GTTTCACCCT TTTAGCCAGG ATGGTCTCGA TCTCCTGACT
```

Fig. 1G

```
8251 TCGTGATCTG CCCGCCTTGG CCTCCCAAAG TGCTAGGATT ACAGGTTTGA

8301 GCCACCGCGC CCGGCCCTGT TTCCTTTTTG TTTGTTCCCC TGATACCCTG

8351 TATCAGGACC AGGAGTCAGT TTGGCGGTTA TGTGTGGGGA AGAAGCTGGG

8401 AAGTCAGGGG CTGTTTCTGT GGACAGCTTT CCCTGTCCTT TGGAAGGCAC

8451 AGAGCTCTCA GCTGCAGGGA ACTAACAGAG CTCTGAAGCC GTTATATGTG

8501 GTCTTCTCTC ATTTCCAGCA GAGCAGGCTC ATATGAATCA ACCAACTGGG

8551 TGAAAAGATA AGTTGCAATC TGAGATTTAA GACTTGATCA GATACCATCT

8601 GGTGGAGGGT ACCAACCAGC CTGTCTGCTC ATTTTCCTTC AGGCTGATCC

8651 CATAATGCAT CCTCAAGTGG TCATCTTAAG CCTCATCCTA CATCTGGCAG

8701 GTAAGTGAGT AGGTGCCCTG GGCGGGAAGA AGGGAGTAGA GGGGGGTTAG

8751 AAGCCAGAGA ATGGGGTAGG GGAAGGGGAG GGGATGGTGG TGGTGGATTA

8801 ATGTAGATGT TCTTTGGGTA CCGTTGTATG GCTATGAGTT AACTAGTGAG

8851 CAGGACCAGA ATAAAGTTTT AGGCCAAAGA AATTGCTTAA CTGCTGTGAA

8901 TTACAACATT CATGGCTAAA TGAACAAGGC AAG
```

Fig. 1H

SEQUENCE LISTING

<160> NUMBER OF SEQ ID NOS: 4

<210> SEQ ID NO 1
<211> LENGTH: 8933
<212> TYPE: DNA
<213> ORGANISM: Homo sapiens

<400> SEQUENCE: 1

```
gatcatacaa acatgctgtt attttatca cttaaaaaaa aaacacccag gattttctcc      60
ttccatttt gcaaaacttt tattttttt ttggaagatg gggactcact ctgtcactca     120
ggctggaatg cagtagtact accatatctc actgcagcct caaactcctg ggctcaagtg     180
atccctcccg cttagcctcc caaatggctg gtactatagg cactcaagtc caactgcttt     240
tctccatgca aactccttga aagtgtttcc tgtattcaat tatctcctga ttttccttct     300
tgtaaacttt ttactgcagt ataaagtact ggggctcact gataatctcc agcttgctca     360
gtctatgaca aatcttattc ctttcctttg cagcatttga ctcatgattg ctgcctgttc     420
tttgatgcgt ttgcttcact tggcttctag gacctttttg cttttctct tacctccttg     480
ggctgcttcc atttctgtat tggtgcctct tccacctcag cattttttt tttttttttt     540
tttaagacgg agtctcgctc tctcgcccag gctggagtgc agtggtgcga tctcggctca     600
ctgcaagctc cgcctcccag gttcacgcca ttctcctgcc tcagcctcct gagtagctgg     660
gactataggc gcccgccacc acgcccggct aatttccacc tcagctttaa caatttttt     720
taaaattaat taatttttt ttttgagacg gagtcttgct ctgtcactca agctggagtg     780
cagtggcatg atctcggctc actgcgacct ctgcctccca ggttcaagca attctcctgc     840
ctcagcctcc tgagtagctg ggattacagg catgcgccat cacacccggc cattttttgt     900
gttttttagta gagacggggt ttcaccatgt tggccaggct ggcctggaac tcctgacctc     960
aagtgatcag cctgccttgg tctcctaaag tgctaagact gcaggtgtga gtcgccacac    1020
ccggccttaa aatttattct tatgtagaga tggtgtttca ccatgttggc caggctgacc    1080
tggaactcct gaccttaagt tatcagcctg ccccggtctc ccaaagtgtt gggattacct    1140
gcatgagtca acatgcttgt cccccatttta atcttttgat gctggaaggc cccaggacct    1200
agtccttagc atcaggcatt cctttgaatc tcatcctttg aattcctacc tcattcaggc    1260
tcctggcttt aaaataccat tttttttttt ttgaggcgga gtctcgctct gtcgcgcagt    1320
ggcgcgatct cagctcactg caagctccgc ctcccaggtt cacaccattc tcctgcctca    1380
gcctcccgag tagctgggac tacaggcacc tgccaccacg cctggctaat tttttgtatt    1440
ttcagtagag acggggtttc atcgtgttac ccagcacagt ctcgatctcg tgatccgccc    1500
acctcggcct cccaaagtgc tgggattaca ggcgtgagcc accgcaccca gccaatacca    1560
tttctaagcc agtaacttgt aactgtatct ttagctcaga cctccctcct gaactccagc    1620
agtctccaca caggtctaag acatgtcaaa ctcaacatac ttaaaaccct gaatatttcc    1680
```

```
tctaaaacct gtggtcatgc aggttttttgt ttttttgtttt ttgttttttt tgagatggag   1740
tcttgctctg ttgcccagac tagagtgcag tgtcacgatc ttggctcact ccaacctctg   1800
cctcctgggt tcaagcaatt ctcctggctc agcctcctga gtagctcaga ttacaggcac   1860
ccacgaccat gcctggctaa attttttgtat ttttagtaga gacagggttt tgccatgttg   1920
gccaggttgg tcttgaactc ctgacctcag gtgatccacc tgccttggcc tcccaaggtg   1980
ttaggattac aggtgtgagc cactgagccc agcctttgca gctctccttg tcttaattgg   2040
ctggaacctc cagctcttcc cgtggctcag gccgaaatcc ttggagtcat cttaggccct   2100
ttctcctcat atcctacagg aaatcctgtt tgctccacct tctccacctc cttggctcaa   2160
gccattctcc tgcctcagcc tctttagtag ctgggactac aagttgcatg ccagcatgcc   2220
tggctaattt ttcttttttct ttcttttttt tttttttttg tagagacagg gtctcactat   2280
gttgccctga gctcctgggc tcaagcagtc ctcccgcctt ggcctcccaa agtccaggga   2340
ttacagctgt gagccatcac atctggctac tctaggttga gtgaggaaag ttcattgacc   2400
acttccactg ctaacccatc tcttctggaa tctttccata gtctcctgac aggtcttcct   2460
gcttctcaat ctagcaacca cagtggtcct tctcaaagga agttagatac tgtcaccta   2520 tgcccttgca gtggtgcttc ttttcatgtg gggtgaaagc ctatgtcctc agaatatggc   2580
tcctaagccc catgtgtctg tcctctgccc tcactcctct gtgatccctg tccctcgctc   2640
tgttgcagtc acgctggcct ctcttgccct gtaaacacac caggcaccct cctgccttag   2700
ggcctttgcc cttcttgtct gtctccatgg aaagcgtttg ctgtcttggc taacttcctt   2760
gtcctttgtc ttagttcaaa taatcacctt cttggtgaaa gtaatagaga ctattcaaac   2820
ctgaccacct tgtttaaaat tgcaactcag tgcctcctca accctccact cccaaccacc   2880
ttcaccctgc tcttgtgtat ccttttgcct tttttgcatt agcattcctc aacttgtaat   2940
atgctgataa attacatttt agtgatgttt taaaaatctg tatatttatt tttcagttaa   3000
aagttagtta catgaggcca ggagtggtgc tcacgcctat aatcccagca ctttgggagg   3060
ccaaggcggg cagatcactt gaggtcagga gttcgtgacc agcctaacca acatggtgaa   3120
accccgtctc tgctaaaatt acaaaaatta gccggtgtgg tgatgcatgc ctgtaatccc   3180
agcttcttgg gaggctgagg taggagaatc gcttgaaccc aggaggcaga gtttgcagtg   3240
agctgagatc gtgccattgc cctccagcct gggcaaaaaa agcgaagctc catctcaaaa   3300
aaaaaaaaaa aaatgtaagt tacatgaggc caggggtctt tggttcattg gtacattcca   3360
gatgaatagg atcatttcta acatatcgca gatcatcaac aaataattgt taaatgagta   3420
cacttttggt attttatat attttctttc tttctttctt tctttctttt tttttttgag   3480
acagaatctc gctctgtcac ccaggctgga gtgcagtggc gtgtgatctc agctcactgc   3540
aacctccacc tcccaggttc aagcgattct cttgcctcag cctccctagt atctgagact   3600
acaggcacgc gccaccacgc ctggctaatt tttgtagttt tagtagagac aggggtttgc   3660
catattggcc aggctggtct tgaactccta acctcaagtg atcctcctgc cttggcctcc   3720
caaagtgctg ggattacagg tgtgagccac catacttggg cttttatgta ttttctatgg   3780
taaacatagg tggtaccctg taattttttat atctttgtaa aagatataaa aaaagaagc   3840 attatattac ttgttatgaa atcagaggag taagtgaagg aaaataacta gcttagggca   3900
gtgggcaggg caggaagaga actgaaaggt aggaagacag ttttggaggg aattgcagaa   3960
gtctggatta tagaggccta atataaagtg atggggatga gggagagact gacaggtaca   4020
atgatgtgga gttggtgagt ccctagttgt ggagggggcc taagaagatc ttgctgtggt   4080
```

-continued

```
gaaagcatgg ggaatatgaa cagctgaact gttttgcagg aggctggagc tggaggtacg    4140
atgtgcgctg agatagcagg gaagtaagtg gtgattgcaa gaaagaacag tgaattattt    4200
tcttttctga attctttctt tttttttgaga caggtgtca atctgttgtc caggctggag    4260
tgcagtggca cgatctcagc tcactgcaac ctccacctcc cgggttcgag caattctcct    4320
gcctcagcct cccaagtagc tgggattaca ggcacccacc accgtgcccg gcccatgttc    4380
tgaatcattt caattcactg ccgttaatct tggtttatac agatgcagct ccctagtgag    4440
cagctggaaa ttcagcttg gtgcccaagt attgtcactt ccagctttac cctacaactg     4500
ggatgcatcc ttcagggggg tcatgaagtt tgccctaaag agtagtgatc cctggaggtt    4560
gtatagctca ttaaaaaaat ccactgtgct atattgtttg ggagtcttta gaacacaggc    4620
gtctctcatg ggagatggtc ctgtgtcaga aaattcaacc ctatggaatt gtacagttat    4680
gtaacatctc agagccttgg ctccacatcc ctgtcctggc tctctctggc tcatcatttc    4740
ctccagttga acaccctcc acccattctt ctcacatgtc acttttaag aaattcttcc       4800 cacccccac attccgtcat caaaatgaat ggtctttccc tatgggtttg tgttccatt       4860 tgtttatcta ttcaattaat aacttttttt tttttgagaa gtctcactct gtggcccagg    4920
ccagagtgca gtggcatgat ctccgctcag ggtaaattct gcctcccggg ttcaggcgat    4980
tctcttgcct cagcctcctg agtagctggg attacaggca cccgccacca cgcctggcta    5040 attttttgcat ttttggtaga gttgggtttc accatgttgg ccaggctggt ttggaaccc    5100 tgacctcaag tgatcctccc acctcggcct cctttggatt acaggtgtga gcaaccatgc    5160
ctggcttcaa cacttaaatt gccttaaagg agtttatggt ctggagttgg gtgccacaca    5220
acacagtcac tatgtgtgac aatttaaatt ttatttttt gttttaatt aatttatttt      5280 tttgaaagct ctgtcatcta aggcttgagt gcagtggtgc catctcaact ccccgaagac    5340
tgtctcctgg gctcaagcaa tctgaaattt taattaaaat gaaattaaat aaaaatttt     5400 aggccaggca tggcggctca cacctgtaat tccagcactt tggaagttg agatgagcgt     5460 atcacttgag gccaggagtt ccagcccagc ctggccaaca tggtgaaact ccacctctgc    5520
taaaaataca aaaattagcc aggcatggtg gcgcgtgtct gtagtcccag ctactcagga    5580
gactgtggca agagaatcac ttaaacccag gagatggagg ttgcactgag ctgagattgt    5640
gacactgcac tccagcctgg gtgacagagt caggctctgt cttggaaaaa aaaaaaatta    5700
aaaatgcctt ggttgcctta gccacatttc aagtgctcaa tagtcatatg tggctagtgg    5760
ctgctgtagt gcacgacact cacacagaat aactctgtaa ccaatattct actggagaca    5820
gaatcgatcc tatggaattc aaattcaaat cctatggaat tgtacagtta tgtaacatct    5880
cagagcactg gctccacatc cctgtcttgg ctctctgtgg ctcatcagtt ccagaataac    5940
tccgttacca gaataactcc attactaaaa ttctaccggg cagcactcta taggagggaa    6000
tagagacaga caccacatat attgcacaca cagataaaat ggattaagga aaacaagata    6060
ataatagtga gagggactgg ttggctactt tagattgaag gacctgtgaa aaatgtccag    6120
ggaggtcata tttaagccgg gataaaaatg aaaaggaaaa aagtgaaaat ggtggggctg    6180
gggagctaga tggagaacac agccacggaa aaggccttag ggttgaggca agttggaaag    6240
aaagctctag tagctggggc tgagtcagca ggggagagag tggtagaaga aatctatggg    6300
gtaggtcagg gccagaccac cagggcttca gtaatttgag taaagattta ggaattatta    6360
ttattattat tattattatt tttctgagag agttatgaga gggttataag tggggaatg     6420
```

```
atgtagtctg attatatatt tacctttacc tcacttatcc tgatttcatt agttgcttac   6480
ttacccatgt ccctgcccga ttgcacaagt ctggattttt gacgtcccta gtatattgag   6540
tcatgtccca tcagctcaat atgttagtaa taactggttg aattgaatta gcttttttt   6600 ttcaatcttt ttttccttaa gaaacagggt cttgctctgt cacccggct ggtgtgcagt   6660 ggcacaatca tagcctccaa ctgctgggct caagcaaccc tcctgcctca gcctcctgag   6720
tagctgggac tacggtcagg tacacaaggc ctgactatat ttttgttcg tttttttgca   6780 gagagggagt cttgctatgt tgcccaggtt ggtctcaaac tccttacctc aggtgatcca   6840
cttgccttgg cctcccaaag tgttgggatt acaggcgtga ccactgtgc ctggcaagaa   6900 atgaattttt atttttattt ttgagatgga gttttgttct tgttgtccag gctagagtgc   6960
aatggcttga tctcggctca ctgcaacctc caccttccag gttcaagcaa ttcttctacc   7020
tcagcctcct aagtagctgg gattacaggc gcccgccacc accccagct aattttgta   7080 tttttagtag agtcggggtt tcaccgtgtt agccaggctg tcttgaact cccgacctca   7140 ggtgactggc ctactcggcc tcccaaagtg ctggggttac aggcacgagc caccatgccc   7200
ggtcaagaaa tgaattttta aacgctgcca tacaaaacac tatgctgaga tcatccactt   7260
ccccatgaac cctgtcatga gctgcaagat acagaccacc actgcctcct ggaagttac   7320 tgaattctta gaccagaaga ggagttaatg aagtactagg caagcttact catgtttgta   7380
tggtttaatg attaacagca gaagtcaaca gcccgattta acgcatgtgg gtgcttgaca   7440
cagagcctgc tatatagtat tctccaaaaa cctcagctag tgctattact gcatatgatg   7500
taggtttagt tttccaagtt cttccgtggc ccttttgct tattatatca atccttggtg   7560
ggagatagag gaagcatttt tagtgctatt ttacaactga ggaaatagag gtttgaagag   7620
aactcaggaa ctctcagggt tacccagcat tgtgagtgac agagcctgga tctgaacgta   7680
agtctgctcc agacttctgt ttcctgaagc attctcttga agtcccttgg taaggaggtg   7740
tagtctgaag catgttgtac aggagcatga aaggttaggc acagtgattc acattcactc   7800
tcaatttctc ttgctaatgg caaacttggc aaatatgactg ttaaggctag ggataagtcg   7860
ttgtggccac tgagtaggaa aagctccacg tccaccagag gcccagttta ctctgaaaag   7920
caagtgcatc tctgccactg gaaggctggc atttgctctc gtgctgccat tgagccacgc   7980
tggttctctg cttccagttt cctttctttt tcttttttt tgttttgttt tttgagacgg   8040
agtcttgctc tgtcgcccag gctggagtgc agtggcgcga tctcggctca ccgcaagctc   8100
cgcctcccgc gggttcacgc cattctcctg cctcagcctc ccgagtagct gggactacag   8160
gcgccagtga ccacgcccgg ctaatttttt gtattttag tagagacggg gtttcaccct   8220
tttagccagg atggtctcga tctcctgact tcgtgatctg cccgccttgg cctcccaaag   8280
tgctaggatt acaggtttga gccaccgcgc ccggccctgt ttcctttttg tttgttcccc   8340
tgataccctg tatcaggacc aggagtcagt ttggcggtta tgtgtgggga agaagctggg   8400
aagtcagggg ctgtttctgt ggacagcttt ccctgtcctt tggaaggcac agagctctca   8460
gctgcaggga actaacagag ctctgaagcc gttatatgtg gtcttctctc atttccagca   8520
gagcaggctc atatgaatca accaactggg tgaaaagata agttgcaatc tgagatttaa   8580
gacttgatca gataccatct ggtggagggt accaaccagc ctgtctgctc attttccttc   8640
aggctgatcc cataatgcat cctcaagtgg tcatcttaag cctcatccta catctggcag   8700
gtaagtgagt aggtgccctg gcgggaaga agggagtaga gggggttag aagccagaga   8760 atgggtagg ggaagggag gggatggtgg tgtggatta atgtagatgt tctttgggta   8820
```

-continued

| | |
|---|---|
| ccgttgtatg gctatgagtt aactagtgag caggaccaga ataaagtttt aggccaaaga | 8880 |
| aattgcttaa ctgctgtgaa ttacaacatt catggctaaa tgaacaaggc aag | 8933 |

<210> SEQ ID NO 2
<211> LENGTH: 4817
<212> TYPE: DNA
<213> ORGANISM: Homo sapiens

<400> SEQUENCE: 2

| | |
|---|---|
| ccctgtaatt tttatatctt tgtaaaagat ataaaaaaaa gaagcattat attacttgtt | 60 |
| atgaaatcag aggagtaagt gaaggaaaat aactagctta gggcagtggg cagggcagga | 120 |
| agagaactga aagtaggaa acagttttg gagggaattg cagaagtctg gattatagag | 180 |
| gcctaatata aagtgatggg gatgagggag agactgacag gtacaatgat gtggagttgg | 240 |
| tgagtcccta gttgtggagg gggcctaaga agatcttgct gtggtgaaag catggggaat | 300 |
| atgaacagct gaactgtttt gcaggaggct ggagctggag gtacgatgtg cgctgagata | 360 |
| gcagggaagt aagtggtgat tgcaagaaag aacagtgaat tattttcttt tctgaattct | 420 |
| ttctttttt tgagacaggg tgtcaatctg ttgtccaggc tggagtgcag tggcacgatc | 480 |
| tcagctcact gcaacctcca cctcccgggt tcgagcaatt ctcctgcctc agcctcccaa | 540 |
| gtagctggga ttacaggcac ccaccaccgt gcccggccca tgttctgaat catttcaatt | 600 |
| cactgccgtt aatcttggtt tatacagatg cagctcccta gtgagcagct ggaaattcag | 660 |
| cttttggtgcc caagtattgt cacttccagc tttaccctac aactgggatg catccttcag | 720 |
| gggggtcatg aagtttgccc taaagagtag tgatccctgg aggttgtata gctcattaaa | 780 |
| aaaatccact gtgctatatt gtttgggagt ctttagaaca caggcgtctc tcatgggaga | 840 |
| tggtcctgtg tcagaaaatt caaccctatg gaattgtaca gttatgtaac atctcagagc | 900 |
| cttggctcca catccctgtc ctggctctct ctggctcatc atttcctcca gttgaaacac | 960 |
| cctccaccca ttcttctcac atgtcacttt ttaagaaatt cttcccaccc cccacattcc | 1020 |
| gtcatcaaaa tgaatggtct ttccctatgg gtttgtgttt ccatttgttt atctattcaa | 1080 |
| ttaataactt tttttttttt gagaagtctc actctgtggc ccaggccaga gtgcagtggc | 1140 |
| atgatctccg ctcagggtaa attctgcctc ccggggttcag gcgattctct tgcctcagcc | 1200 |
| tcctgagtag ctgggattac aggcacccgc caccacgcct ggctaatttt tgcattttg | 1260 |
| gtagagttgg gtttcaccat gttggccagg ctggtttgga accctgacc tcaagtgatc | 1320 |
| ctcccacctc ggcctccttt ggattacagg tgtgagcaac catgcctggc ttcaacactt | 1380 |
| aaattgcctt aaaggagttt atggtctgga gttgggtgcc acacaacaca gtcactatgt | 1440 |
| gtgacaattt aaattttatt tttttgtttt taattaattt attttttga aagctctgtc | 1500 |
| atctaaggct tgagtgcagt ggtgccatct caactccccg aagactgtct cctgggctca | 1560 |
| agcaatctga aatttaatt aaaatgaaat taaataaaaa ttttaggcc aggcatggcg | 1620 |
| gctcacacct gtaattccag cacttttgga agttgagatg agcgtatcac ttgaggccag | 1680 |
| gagttccagc ccagcctggc caacatggtg aaactccacc tctgctaaaa atacaaaaat | 1740 |
| tagccaggca tggtggcgcg tgtctgtagt cccagctact caggagactg tgcaagaga | 1800 |
| atcacttaaa cccaggagat ggaggttgca ctgagctgag attgtgacac tgcactccag | 1860 |
| cctgggtgac agagtcaggc tctgtcttgg aaaaaaaaaa aattaaaaat gccttggttg | 1920 |
| ccttagccac atttcaagtg ctcaatagtc atatgtggct agtggctgct gtagtgcacg | 1980 |

-continued

```
acactcacac agaataactc tgtaaccaat attctactgg agacagaatc gatcctatgg    2040
aattcaaatt caaatcctat ggaattgtac agtatgtaa catctcagag cactggctcc     2100
acatccctgt cttggctctc tgtggctcat cagttccaga ataactccgt taccagaata    2160
actccattac taaaattcta ccgggcagca ctctatagga gggaatagag acagacacca    2220
catatattgc acacacagat aaaatggatt aaggaaaaca agataataat agtgagaggg    2280
actggttggc tactttagat tgaaggacct gtgaaaaatg tccagggagg tcatatttaa    2340
gccgggataa aaatgaaaag gaaaaaagtg aaaatggtgg ggctggggag ctagatggag    2400
aacacagcca cggaaaaggc cttagggttg aggcaagttg gaaagaaagc tctagtagct    2460
ggggctgagt cagcagggga gagagtggta gaagaaatct atggggtagg tcagggccag    2520
accaccaggg cttcagtaat ttgagtaaag atttaggaat tattattatt attattatta    2580 ttattttttct gagagagtta tgagagggtt ataagtgggg gaatgatgta gtctgattat    2640
atatttacct ttacctcact tatcctgatt tcattagttg cttacttacc catgtccctg    2700
cccgattgca caagtctgga ttttttgacgt ccctagtata ttgagtcatg tcccatcagc   2760
tcaatatgtt agtaataact ggttgaattg aattagcttt tttttttcaa tcttttttttc   2820 cttaagaaac agggtcttgc tctgtcaccc cggctggtgt gcagtggcac aatcatagcc    2880
tccaactgct gggctcaagc aaccctcctg cctcagcctc ctgagtagct gggactacgg    2940
tcaggtacac aaggcctgac tatatttttt gttcgttttt ttgcagagag ggagtcttgc    3000
tatgttgccc aggttggtct caaactcctt acctcaggtg atccacttgc cttggcctcc    3060
caaagtgttg ggattacagg cgtgagccac tgtgcctggc aagaaatgaa tttttatttt    3120
tatttttgag atggagtttt gttcttgttg tccaggctag agtgcaatgg cttgatctcg    3180
gctcactgca acctccacct tccaggttca agcaattctt ctacctcagc tcctaagta     3240 gctgggatta caggcgcccg ccaccacccc cagctaattt ttgtattttt agtagagtcg    3300
gggtttcacc gtgttagcca ggctggtctt gaactcccga cctcaggtga ctggcctact    3360
cggcctccca aagtgctggg gttacaggca cgagccacca tgcccggtca agaaatgaat    3420
ttttaaacgc tgccatacaa aacactatgc tgagatcatc cacttcccca tgaaccctgt    3480
catgagctgc aagatacaga ccaccactgc ctccttggaa gttactgaat tcttagacca    3540
gaagaggagt taatgaagta ctaggcaagc ttactcatgt ttgtatggtt taatgattaa    3600
cagcagaagt caacagcccg atttaacgca tgtgggtgct tgacacagag cctgctatat    3660
agtattctcc aaaaacctca gctagtgcta ttactgcata tgatgtaggt ttagttttcc    3720
aagttcttcc gtggcccttt ttgcttatta tatcaatcct tggtgggaga tagaggaagc    3780 attttttagtg ctattttaca actgaggaaa tagaggtttg aagagaactc aggaactctc   3840
agggttaccc agcattgtga gtgacagagc ctggatctga acgtaagtct gctccagact    3900
tctgtttcct gaagcattct cttgaagtcc cttggtaagg aggtgtagtc tgaagcatgt    3960
tgtacaggag catgaaaggt taggcacagt gattcacatt cactctcaat ttctcttgct    4020
aatggcaaac ttggcaatat gactgttaag gctaggata agtcgttgtg ccactgagt     4080 aggaaaagct ccacgtccac cagaggccca gtttactctg aaaagcaagt gcatctctgc    4140
cactggaagc ctggcatttg ctctcgtgct gccattgagc cacgctggtt ctctgcttcc    4200
agtttccttt tcttttctt tttttttgttt tgttttttga gacggagtct gctctgtcg    4260 cccaggctgg agtgcagtgg cgcgatctcg gctcaccgca agctccgcct cccgcgggtt    4320
cacgccattc tcctgcctca gcctcccgag tagctgggac tacaggcgcc agtgaccacg    4380
```

```
cccggctaat ttttttgtatt tttagtagag acgggggtttc acccttttag ccaggatggt    4440
ctcgatctcc tgacttcgtg atctgcccgc cttggcctcc caaagtgcta ggattacagg     4500
tttgagccac cgcgcccggc cctgtttcct ttttgtttgt tccctgata ccctgtatca      4560 ggaccaggag tcagtttggc ggttatgtgt ggggaagaag ctgggaagtc agggggctgtt   4620 tctgtggaca gctttccctg tcctttggaa ggcacagagc tctcagctgc agggaactaa    4680
cagagctctg aagccgttat atgtggtctt ctctcatttc cagcagagca ggctcatatg    4740
aatcaaccaa ctgggtgaaa agataagttg caatctgaga tttaagactt gatcagatac    4800
catctggtgg agggtac                                                   4817
```

<210> SEQ ID NO 3
<211> LENGTH: 1291
<212> TYPE: DNA
<213> ORGANISM: Homo sapiens

<400> SEQUENCE: 3

```
gaattcttag accagaagag gagttaatga agtactaggc aagcttactc atgtttgtat     60
ggtttaatga ttaacagcag aagtcaacag cccgatttaa cgcatgtggg tgcttgacac    120
agagcctgct atatagtatt ctccaaaaac ctcagctagt gctattactg catatgatgt    180
aggtttagtt ttccaagttc ttccgtggcc cttttttgctt attatatcaa tccttggtgg   240
gagatagagg aagcattttt agtgctattt tacaactgag gaaatagagg tttgaagaga    300
actcaggaac tctcagggtt acccagcatt gtgagtgaca gagcctggat ctgaacgtaa    360
gtctgctcca gacttctgtt tcctgaagca ttctcttgaa gtcccttggt aaggaggtgt    420
agtctgaagc atgttgtaca ggagcatgaa aggttaggca cagtgattca cattcactct    480
caatttctct tgctaatggc aaacttggca atatgactgt taaggctagg gataagtcgt    540
tgtggccact gagtaggaaa agctccacgt ccaccagagg cccagtttac tctgaaaagc    600
aagtgcatct ctgccactgg aaggctggca tttgctctcg tgctgccatt gagccacgct    660
ggttctctgc ttccagtttc cttttctttt ctttttttt gttttgtttt ttgagacgga     720
gtcttgctct gtcgcccagg ctggagtgca gtggcgcgat ctcggctcac cgcaagctcc    780
gcctcccgcg ggttcacgcc attctcctgc ctcagcctcc cgagtagctg ggactacagg    840
cgccagtgac cacgcccggc taatttttttg tattttttagt agagacgggg tttcacccctt   900 ttagccagga tggtctcgat ctcctgactt cgtgatctgc ccgccttggc ctcccaaagt    960
gctaggatta caggtttgag ccaccgcgcc cggccctgtt tccttttttgt ttgttcccct  1020 gatacccctgt atcaggacca ggagtcagtt tggcggttat gtgtggggaa gaagctggga  1080
agtcaggggc tgtttctgtg gacagctttc cctgtccttt ggaaggcaca gagctctcag   1140
ctgcagggaa ctaacagagc tctgaagccg ttatatgtgg tcttctctca tttccagcag   1200
agcaggctca tatgaatcaa ccaactgggt gaaaagataa gttgcaatct gagatttaag   1260
acttgatcag ataccatctg gtggagggta c                                  1291
```

<210> SEQ ID NO 4
<211> LENGTH: 503
<212> TYPE: DNA
<213> ORGANISM: Homo sapiens

<400> SEQUENCE: 4

```
cggggttcacg ccattctcct gcctcagcct cccgagtagc tgggactaca ggcgccagtg    60
```

-continued

| | | | | |
|---|---|---|---|---|
| accacgcccg | gctaattttt | tgtattttta | gtagagacgg | ggtttcaccc | ttttagccag | 120 |
| gatggtctcg | atctcctgac | ttcgtgatct | gcccgccttg | gcctcccaaa | gtgctaggat | 180 |
| tacaggtttg | agccaccgcg | cccggccctg | tttccttttt | gtttgttccc | ctgataccct | 240 |
| gtatcaggac | caggagtcag | tttggcggtt | atgtgtgggg | aagaagctgg | gaagtcaggg | 300 |
| gctgtttctg | tggacagctt | tccctgtcct | ttggaaggca | cagagctctc | agctgcaggg | 360 |
| aactaacaga | gctctgaagc | cgttatatgt | ggtcttctct | catttccagc | agagcaggct | 420 |
| catatgaatc | aaccaactgg | gtgaaaagat | aagttgcaat | ctgagattta | agacttgatc | 480 |
| agataccatc | tggtggaggg | tac | | | | 503 |

RENAL REGULATORY ELEMENTS AND METHODS OF USE THEREOF

CROSS REFERENCE TO RELATED APPLICATIONS

This application is a national phase filing under 35 U.S.C. § 371 of international application number PCT/US01/19295, filed Jun. 15, 2001, which claims the benefit of priority of provisional application No. 60/212,131, filed Jun. 16, 2000.

STATEMENT OF GOVERNMENT INTEREST

This invention was made with federal government support under grant #DK 39773. The United States government has certain rights in the invention.

FIELD OF THE INVENTION

The invention relates generally to nucleic acids and more particularly to nucleic acids which can be used to direct expression in renal tissue of operably linked sequences.

BACKGROUND OF THE INVENTION

Significant interruption in kidney function in an individual can lead to incapacitation or even death. Disease or injury can impair kidney function. An example of an injury that can damage kidneys is ischemic injury. In this type of injury, kidney tissue is damaged because of oxygen deprivation occurring as a result of interruption of blood flow to the kidneys.

Certain agents involved in repair of diseased or damaged kidney tissue, and mechanisms in which the repair takes place, have been described. Mechanisms include induction of gene expression and recruitment of growth factors to the affected kidney tissue. Cell death and cellular proliferation are also associated with repair or kidney tissue.

Agents implicated in kidney tissue repair include polypeptides, e.g., growth factors such as insulin growth factor (IGF), epidermal growth factor (EGF), hepatocyte growth factor (HGF), and the endothelial cell adhesion molecule ICAM-1.

Recently, the polypeptide kidney-injury molecule (KIM-1) has been described. The expression of KIM-1 is increased in injured kidney tissue. The rat and human forms of this protein have been characterized. The KIM-1 cDNA sequence reveals that the KIM-1 protein is a type 1 membrane protein that contains a novel six-cysteine immunoglobulin-like domain and a mucin domain. The KIM-1 protein is a member of the immunoglobulin gene superfamily and most closely resembles mucosal addressin cell adhesion molecule 1 (MAdCAM-1).

SUMMARY OF THE INVENTION

It has been discovered that nucleic acid sequences in the vicinity of the human KIM-1 gene can be used to express linked sequences in renal tissue. Accordingly, the invention provides a cis-acting regulatory element useful for, inter alia, directing expression of an operatively linked sequence, e.g., a gene, in a mammal. The cis-acting KIM-1 regulatory sequence can also be used to identify trans-acting factors that mediate the response of the kidney to damaged or diseased tissue.

The invention provides an isolated nucleic acid that includes a cis-acting KIM-1 derived regulatory sequence.

The nucleic acid can be, e.g., a nucleic acid sequence that includes the nucleic acid sequence of SEQ ID NOs:1, 2 or 3. The nucleic acid includes at least 5 contiguous nucleotides from a sequence that hybridizes to SEQ ID NOs: 1, 2, or 3, or sequences complementary to SEQ ID NOs: 1, 2, or 3. For example the regulatory sequence can include between 5 and 35 contiguous nucleotides from SEQ ID NO:3, or sequences complementary to such portions of SEQ ID NO:3.

In some embodiments, a cis-acting KIM-1 regulatory sequence according to the invention includes a portion of SEQ ID NOs:1, 2 or 3 sufficient to regulate kidney tissue-specific transcription of an operably linked sequence, e.g., an operably linked polypeptide-encoding sequence. A cis-acting KIM-1 regulatory sequence according to the invention can include a portion of SEQ ID NOs:1, 2 or 3 is sufficient to regulate kidney tissue-specific transcription following cellular injury e.g., anoxia or exposure to reactive oxygen species ("ROS"), or in a cell present in a confluent population of cells.

The invention also provides a cis-acting KIM-1 regulatory sequence operably linked to a sequence encoding a KIM-1 antisense nucleic acid. The cis-acting KIM-1 regulatory sequence can be operably linked to at least one polypeptide-encoding sequence and regulates renal tissue-specific transcription of the polypeptide-encoding sequence. For example, the polypeptide-encoding sequence may encode a KIM-1 polypeptide (e.g., a human KIM-1 polypeptide), or a non-KIM-1 polypeptide. This polypeptide can be, e.g., a cell survival-promoting factor, a cell growth-promoting factor, a wound-healing factor, an anti-fibrotic factor, an apoptosis-inhibiting factor, an anti-inflammatory factor, a terminal differentiation-promoting factor, a cell growth-inhibiting factor, an intravascular-volume restoration factor, a chelating agent, an alkylating agent, an angiotensin-converting enzyme-inhibiting factor, erythropoietin, a cytokine, a receptor, an anticoagulant, an enzyme, a hormone, an antibody, or a renal structural protein.

A cis-acting KIM-1 regulatory sequence according to the invention may be linked to, e.g., nucleic acid sequences encoding insulin growth factor (IGF), an epidermal growth factor (EGF), a fibroblast growth factor (FGF), a transforming growth factor beta (TGF β) Type II receptor, a hepatocyte growth factor (HGF), or an endothelial cell adhesion molecule ICAM-1.

The invention also provides a vector that includes a nucleic acid comprising a cis-acting KIM-1 regulatory sequence and cells containing these nucleic acids and vectors. The cell can be prokaryotic or eukaryotic. The cell can be, e.g., a metazoan organism or a unicellular organism, and can include, e.g., a fungal cell, yeast cell (such as *Saccharomyces, Schizosaccharomyces,* or *Candida* spp.), or a mammalian cell, e.g., a human, canine, bovine, porcine, feline, or rodent cell, or a non-human mammalian embryonic blastocyst cell.

The invention also provides a transgenic non-human mammal, e.g., a mouse, rat, goat, pig, cow, or sheep, containing an isolated cis-acting KIM1 regulatory sequence. The transgenic animal can be produced, e.g., by intrauterine implantation of a blastocyte cell containing a cis-acting KIM-1 regulatory sequence. The invention also includes one or more progeny of the transgenic non-human mammal DNA, wherein the progeny comprises the cis-acting DNA, or a fragment thereof.

The invention also provides a method of directing expression of a polypeptide. The method includes providing a cell, e.g., a renal cell, that includes an isolated cis-acting KIM-1 regulatory sequence operably linked to sequence encoding a polypeptide of interest, culturing the cell under conditions that allow for the expression of the polypeptide and expressing the polypeptide-encoding sequence.

The invention also includes a method of increasing transcription of a polypeptide-encoding sequence in tissue. The method includes providing a cell in the tissue that includes a cis-acting KIM-1 regulatory sequence linked to the polypeptide-encoding sequence and culturing the cell under conditions that allow for the transcription of the polypeptide-encoding sequence. The polypeptide-encoding sequence is then expressed, resulting in transcription of the polypeptide-encoding sequence in the tissue.

The invention also includes a method for identifying a test compound that modulates expression from a cis-acting KIM-1 derived regulatory sequence. The test compound can be contacted with a reporter construct that includes a reporter gene operably linked to an isolated cis-acting KIM-1 regulatory sequence. The level of expression of the reporter gene in the tissue is detected, e.g., measured. A change in the level of expression in the presence of the test compound relative to the level of expression in the absence of the test compound indicates that the test compound modulates the activity of the KIM promoter.

The invention also provides a method for delivering a therapeutic polypeptide to renal tissue of a subject. The method includes providing in the renal tissue a cell that includes a cis-acting KIM-1 regulatory sequence operably linked to a therapeutic polypeptide, and culturing the cell under conditions that allow for the expression of the polypeptide. The polypeptide-encoding sequence is expressed, thereby delivering the therapeutic polypeptide to the renal tissue of the subject.

The invention also includes a method for treating or preventing renal tissue injury. The method includes providing a cell that includes cis-acting KIM-1 regulatory sequence operably linked to a polypeptide coding sequence, and culturing the cell under conditions that allow for the expression of a therapeutic polypeptide-encoding sequence. The therapeutic polypeptide-encoding sequence is expressed, and the expressed polypeptide contacts the renal tissue, thereby treating or preventing renal tissue injury.

The invention also includes a method for increasing transcription of a nucleic acid in a subject by administering to the subject a cis-acting KIM-1 regulatory sequence operably linked to the nucleic acid and allowing for expression of the operably linked nucleic acid.

The invention also provides a method for treating or preventing renal tissue injury in a subject by administering to a subject in need thereof a cis-acting KIM-1 regulatory sequence operably linked to a sequence encoding a therapeutic polypeptide, in an amount sufficient to treat or prevent renal tissue injury in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A–H are schematic representations of a nucleic acid sequence that includes a cis-acting KIM-1 regulatory sequence (SEQ ID NO:1).

DETAILED DESCRIPTION OF THE INVENTION

Figure 2A:
FIGS. 2A–D are schematic representations of sequences from the 5' region of the human KIM-1 gene.

The invention provides a cis-acting regulatory element useful for, inter alia, directing expression of an operatively linked sequence, e.g., a gene, in a mammal. This cis-acting regulatory sequence from KIM-1 can also be used to identify trans-acting factors that mediate the response of the kidney to damaged or diseased tissue.

Sequence Identifier Numbers (SEQ ID NOs)

Sequence identifier numbers used herein include the following:

SEQ ID NO:1 corresponds to the nucleotide sequence of an 8933 bp human genomic DNA from the 5' region of KIM-1 gene and is disclosed in FIGS. 1A–H. This fragment is present as a BamH1-BamH1 insert in the BamH1 site of the EMBL3 phage vector. The construct is named MZ007.

SEQ ID NO:2 corresponds to the nucleotide sequence of a 4.8 kb KpnI-KpnI fragment encompassing nucleotides 3796 to 8612 of the human KIM-1 insert in MZ007.

SEQ ID NO:3 corresponds to the nucleotide sequence of a 1.3 kb EcoR1-KpnI fragment encompassing nucleotides 7322–8612 of human KIM-1 insert in MZ007.

SEQ ID NO:4 corresponds to the nucleotide sequence of a 0.5 kb SacII-KpnI fragment encompassing nucleotides 8110–8612 of human KIM-1 insert in MZ007.

Cis-acting KIM-1 Derived Regulatory Sequences

Included in the invention is an isolated DNA that includes a cis-acting KIM-1 derived regulatory sequence. The term "isolated" refers to molecules separated from other DNA or RNA molecules, present in the natural source of the regulatory sequence. The term also refers to a nucleic acid or peptide that is substantially free of cellular material, viral material, or culture medium when produced by recombinant DNA techniques, or chemical precursors or other chemicals when chemically synthesized. An isolated nucleic acid includes nucleic acid fragments that are not naturally occurring as fragments and would not be found in the natural state. The term "isolated" is also used herein to refer to polypeptides that are isolated from other cellular proteins, and the term is meant to encompass both purified and recombinant polypeptides.

A cis-acting KIM-1 derived regulatory sequence, also termed herein "cis-acting regulatory element", "regulatory element", or "regulatory sequence", includes nucleic acid sequence elements derived from sequences in the vicinity of a mammalian KIM-1 gene that are capable of modulating transcription from a basic promoter, as well as enhancers or silencers. The terms "promoter" and "regulatory element" further encompass "tissue specific" promoters and regulatory elements, i.e., promoters and regulatory elements which bring about expression of an operably linked DNA sequence preferentially in specific cells (e.g., cells of a renal tissue). Gene expression occurs preferentially in a specific cell if expression in this cell type is significantly higher than expression in other cell types. The terms "promoter" and "regulatory element" also encompass so-called "leaky" promoters and "regulatory elements", which regulate expression of a selected DNA primarily in one tissue, but cause expression in other tissues as well. The terms "promoter" and "regulatory element" also encompass non-tissue specific promoters and regulatory elements, i.e., promoters and regulatory elements which are active in most cell types.

A promoter or regulatory element can be a constitutive promoter or regulatory element, i.e., a promoter or regulatory element which constitutively regulates transcription, or it can be a promoter or regulatory element which is inducible, i.e., a promoter or regulatory element which is active primarily in response to a stimulus. A stimulus can be, e.g., a physical stimulus, such as injury (e.g., ischemia), and/or a molecule, such as a hormone, a cytokine, a heavy metal, phorbol esters, cyclic AMP (cAMP), or retinoic acid.

The term "enhancer", also referred to herein as "enhancer element", includes regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. The terms "promoter" and "regulatory element" further encompass "tissue specific" promoters and regulatory elements, i.e., promoters and regulatory elements which effect expression of the selected DNA sequence preferentially in specific cells (e g., cells of a specific tissue). Gene expression occurs preferentially in a specific cell if expression in this cell type is significantly higher than expression in other cell types.

In some embodiments, one or more copies of a cis-acting regulatory element is present within a transcribed region of a KIM-1 gene. In other embodiments, the cis-acting regulatory element is located 5' to the transcriptional start site of a KIM-1 gene.

In some embodiments, a cis-acting regulatory sequence is operably linked sequence to a promoter that is not derived from the native KIM-1 gene, and to a heterologous sequence, such as a polypeptide-encoding sequence. In other embodiments, the cis-acting regulatory sequence is operably linked to a KIM-1 promoter sequence and a heterologous sequence, such as a polypeptide-encoding sequence.

In some embodiments, the cis-acting regulatory sequence includes the 1.3 kb sequence of SEQ ID NO:3, e.g., the regulatory sequence can include the nucleotides of SEQ ID NO:1 and SEQ ID NO:2, as well as SEQ ID NO:3. In other embodiments, the cis-acting regulatory sequence includes a portion of SEQ ID NO:3 that is sufficient to confer renal tissue expression of an operably linked sequence which otherwise would not be expressed in renal tissue. For example, the cis-acting regulatory sequence may include at least 5, 10, 15, 20, 25, 30, 35, 50, 100, 125, or 150 contiguous nucleotides from SEQ ID NO:3, or sequences complementary to SEQ ID NO:3. Thus, if desired, sequences responsible for conferring renal cell-specific expression in the sequence of SEQ ID NO:3 can be localized more precisely. Localization can be performed using methods well-known in the art, e.g., by constructing plasmids containing successively smaller portions of the 1.3 kb fragment of SEQ ID NO:3 placed upstream of a luciferase reporter gene in a construct such as pGL3 Basic (Promega Corporation, Madison, Wis.), or in any of the many reporter genes known in the art. The construct is then transfected into kidney cells. Suitable kidney cells include, e.g., COS, LLC/PK1, and MDCK cells. Increased expression of the reporter gene in kidney cells compared to the expression of the starting construct alone indicates that the smaller test fragment of the 1.3 kb DNA allows for renal tissue expression. Higher expression of the test fragment in renal tissue as compared to other cell types (i.e., fibroblast cells or non-smooth muscle cells) indicates that the DNA directs polypeptide expression in a renal tissue-specific manner.

Similarly, in other embodiments, the cis-acting regulatory sequence is sufficient to confer both inducible (e.g., upon exposure to a stimulus) and tissue-specific expression in injured renal tissue. For example, the sequence can include at least the portion or portions of SEQ ID NO: 2 that are necessary and sufficient for such expression. Such portion(s) can be localized routinely as described above.

KIM-1 cis-sequences according to the invention can be used to direct expression of linked sequences following injury or under various conditions. For example, a nucleotide sequence that includes SEQ ID NO:2 (the 4.8 kb KpnI-KpnI fragment) can be used to direct expression of a linked polypeptide in cells that have been subjected to injury using a reactive oxygen species ("ROS"), or subjected to injury because of anoxia. A nucleotide sequence that includes at least the relevant portion or portions of SEQ ID NO:2 can also be used to direct expression of a sequence of interest in confluent cells.

In another embodiment, the isolated nucleic acid includes a cis-acting KIM-1 derived regulatory sequence that has been modified, e.g., by adding, deleting, or substituting one or more nucleic acid residues. Such modifications can modulate the regulatory or transcriptional activity of the regulatory element. For example, a modification can increase or decrease the activity of a promoter or regulatory element. A modification can also affect the tissue specificity or inducibility of a promoter or regulatory element.

Desired modifications of a regulatory element according to the present invention can be performed according to methods well known in the art, such as by mutagenesis. The activity of the modified promoter or regulatory element can then be tested, using the herein described methods for assaying the cis-acting activity of a KIM-1 regulatory sequence.

In some embodiments, the regulatory sequence is inducible. As used herein, "inducible" means that the regulatory sequence affects expression of a linked sequence in response to a stimulus. The stimulus can be physical, e.g., stress, such as heat shock, anoxia, or pressure, or chemical. Examples of chemical stimuli include, e.g., a hormone, a cytokine, a heavy metal, phorbol esters, cyclic AMP (cAMP), or retinoic acid. In preferred embodiments, the regulatory sequence is inducible by injury, e.g., ischemic injury, or ischemia. As used herein, "ischemia" means having a blood flow at least 10% below that which is normal for an individual of similar size and age, as measured under resting conditions or exercise conditions. In an adult human, normal resting blood flow is approximately 1 ml/min/gram of myocardial mass. During exercise, blood flow typically rises to approximately 3–6 ml/min/gram of myocardial mass. Ischemia may be associated with a physical would or blow, sudden loss of blood volume, toxicity, or a physical obstruction such as a tumor.

Other types of injury include, e.g., injury due to hypertension, chemotherapy (e.g., injury due to cisplatin damage), chronic renal failure, injury due to auto-immune disorders (e.g., lupus), or polycystic kidney (PCK) disease.

In some embodiments, the regulatory sequence preferentially directs expression of an operably linked sequence in renal tissue. The term "operably linked" means that the regulatory sequence is associated with the nucleic acid in such a manner as to facilitate transcription of the nucleic acid. In some embodiments, the operably linked nucleic acid encodes an antisense nucleic acid. The antisense nucleic acid can be a portion of the anti-sense strand of a gene whose expression is intended to be decreased in a renal tissue. For example, for conditions characterized by undesired proliferation of kidney tissue, the DNA may be a KIM-1 antisense nucleic acid.

In other embodiments, the DNA is operably linked to at least one polypeptide-encoding sequence. The polypeptide sequence can be, e.g., one encoded by a KIM-1 cDNA. Examples of nucleic acids encoding rat and human KIM-1 cDNAs, and their corresponding encoded amino acid sequences are provided in PCT publication WO97/44460.

Alternatively, the DNA is operably linked to nucleic acid that encodes a polypeptide other than KIM-1. For example, the polypeptide can be a therapeutic factor such as insulin growth factor (IGF), epidermal growth factor (EGF), fibroblast growth factor (FGF), transforming growth factor beta (TGF β) Type II receptor, particularly the soluble fragment of TGF β receptor, hepatocyte growth factor (HGF), and the endothelial cell adhesion molecule ICAM-1. Other therapeutic polypeptides include factors such as a cell survival-promoting factor, a cell growth-promoting factor, a wound-healing factor, an anti-fibrotic factor, an apoptosis-inhibiting factor, an anti-inflammatory factor, a terminal differentiation-promoting factor, a cell growth-inhibiting factor, an intravascular-volume restoration factor, a chelating agent, an alkylating agent, an angiotensin-converting enzyme-inhibiting factor, erythropoietin, a cytokine, a receptor, an anticoagulant, an enzyme, a hormone, an antibody, and a renal structural protein.

A nucleic acid to be transcribed from a KIM-1 derived regulatory element can also be linked to a reporter gene. A reporter gene is any gene encoding a protein, the amount of which can be determined. Exemplary reporter genes include the luciferase gene, e.g., the bacterial luciferase gene, e.g., the luciferase gene present in pGL3-basic (Promega Corp., Madison, Wis.). Other suitable reporter genes include the beta-galactosidase gene (LacZ), the chloramphenicol acetyl transferase (CAT) gene, or any gene encoding a protein providing resistance to a specific drug.

The regulatory elements disclosed herein can also be used to prepare probes and primers based on KIM-1 derived regulatory sequences. These probes and primers can be used, e.g., to identify KIM-1 genomic regions in a subject, such as a human. The probes can be provided in the form of a probe or primer that includes a region of nucleotide sequence that hybridizes under stringent conditions to at least approximately 6, 8, 10 or 12, preferably about 25, 30, 40, 50 or 75 consecutive nucleotides of any of SEQ ID NOS: 1, 2, 3, or 4.

The probe optionally includes an attached label, which is capable of being detected. The label can be, e.g., radioisotopes, fluorescent moieties, enzymes, and enzyme co-factors.

The cis-acting regulatory sequences, including the probe or primer molecules, can also be used as a part of a diagnostic test kit, for example, to detect mutations in the promoter, which result in faulty expression of a renal gene or a gene associated with renal tissue.

Nucleic acids, including nucleic acid fragments, containing or derived from cis-acting KIM-1 regulatory sequences can be prepared according to methods well known in the art and described, e.g., in Sambrook, J. Fritsch, E. F., and Maniatis, T. (1989) MOLECULAR CLONING: A LABORATORY MANUAL, Cold Spring Harbor Laboratory Press, Cold Spring Harbor, N.Y. For example, discrete fragments of the regulatory element can be prepared and cloned using restriction enzymes. Alternatively, discrete fragments can be prepared using the Polymerase Chain Reaction (PCR) using primers having an appropriate sequence, such as a sequence in SEQ ID NO: 1. The activity of promoter fragments can be tested in vitro in transfection assays or in vivo in transgenic animals described herein. Also within the scope of the invention are nucleic acids that are homologues or equivalents of the above-described nucleic acids.

Cis-acting KIM-1 derived regulatory sequences can be isolated from other organisms by using a KIM-1 cDNA to screen genomic DNA sequences in the organism of interest, and then testing the genomic sequences in promoter-reporter assays as described herein. Preferably, the KIM-1 cDNA used for the screening is from the same, or closely related organism. Thus, to isolate a murine KIM-1 derived cis-regulatory sequence, the murine KIM-1 cDNA is used. Preferably, the probe is derived from a 5' region of the KIM-1 cDNA.

Vectors and Cells Containing Cis-acting KIM-1 Derived Regulatory Sequences

This invention also provides vectors, e.g., expression vectors that include cis-acting KIM-1 derived regulatory sequences.

In some embodiments, the expression vector includes a recombinant gene encoding a KIM-1 or a therapeutic polypeptide. Such expression vectors can be used to transfect cells and thereby produce protein. Constructs containing cis-acting KIM-1 derived regulatory sequences can also be used as a part of a gene therapy protocol to deliver nucleic acids in vitro or in vivo to particular cell types (e.g., kidney).

The vector can include any vector known in the art for propagating a desired nucleic acid in a cell of interest. Thus, the vector can be chosen to propagate a nucleic acid that includes a cis-acting KIM-1 derived regulatory sequences in a prokaryotic or eukaryotic host, or both. In some embodiments, the vector is a viral vector, e.g., a retroviral vector. For a review, see Miller, A. D. (1990) *Blood* 76:271. Protocols for producing recombinant retroviruses and for infecting cells in vitro or in vivo with such viruses can be found, e.g., in CURRENT PROTOCOLS IN MOLECULAR BIOLOGY, Ausubel, F. M. et al. (eds.) Greene Publishing Associates, (1989), Sections 9.10–9.14 and other standard laboratory manuals. Examples of suitable retroviruses include pLJ, pZIP, pWE and pEM.

Vectors can alternatively be adenovirus-derived vectors, e.g., those described in Berkner et al. (1988) *BioTechniques*

6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art.

The vector can be derived from an adeno-associated virus (AAV). Adeno-associated virus is a naturally occurring defective virus that requires another virus, such as an adenovirus or a herpes virus, as a helper virus for efficient replication and a productive life cycle. For a review see Muzyczka et al. *Curr. Topics in Micro. and Immunol.* (1992) 158:97–129. It is also one of the few viruses that can integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). See also U.S. Pat. No. 5,872,154. Other suitable vectors include those based in the human immunodeficiency virus (HIV). These vectors are described in, e.g., U.S. Pat. Nos. 5,665,577 and 5,981,276.

Vectors can be introduced into cells using methods known in the art. In addition to viral transfer methods, such as those illustrated above, non-viral methods can also be used to introduce a gene. These methods include, e.g., calcium phosphate precipitation, microparticle-mediated delivery, and biolistic transformation. In some embodiments, delivery can rely on endocytic pathways for the uptake of genes by the targeted cell. Exemplary targeting means of this type include liposomal derived systems, poly-lysine conjugates, and artificial viral envelopes.

Delivery can be performed using nucleic acids entrapped in liposomes bearing positive charges on their surface (e.g., lipofectins) and (optionally) which are tagged with antibodies against cell surface antigens of the target tissue. See, e.g., Mizuno et al. (1992) *No Shinkei Geka* 20:547–551; PCT publication WO91/06309; Japanese patent application 1047381; and European patent publication EP-A-43075. For example, lipofection of cells can be carried out using liposomes tagged with monoclonal antibodies against any cell surface antigen present on a hepatic cell, such as an asialoglycoprotein receptor.

Cells containing cis-acting KIM-1 regulatory sequences, or vectors that include cis-acting KIM-1 regulatory sequences as described herein, can be any cell known in the art. Thus, they can include prokaryotic cells (e.g., *E. coli* cells) or eukaryotic calls. Eukaryotic cells can include single-celled organisms such, e.g. yeast (e.g., *Saccharomyces cerevisiae* or *Schizosaccharomyces pombe*). Alternatively, the cells can be mammalian cells, e.g., human or simian cells. In some embodiments, the cells are kidney cells, or cell lines derived from kidney cells.

Transgenic Animals Containing Cis-acting KIM-1 Regulatory Sequences

The invention also includes transgenic non-human vertebrates, e.g., mammals and birds, that contain cis-acting KIM-1 regulatory sequences.

For example, some embodiments, a host cell of the invention is a fertilized oocyte or an embryonic stem cell into which exogenous cis-acting KIM-1 regulatory sequences have been introduced. Such host cells can be used to create non-human transgenic vertebrate animals in which exogenous cis-acting KIM-1 regulatory sequences have been introduced into their genome or homologous recombinant animals in which endogenous cis-acting KIM-1 regulatory sequences have been altered. Such animals are useful for studying the function and/or activity of cis-acting KIM-1 regulatory sequences and for identifying and/or evaluating modulators of cis-acting KIM-1 regulatory sequences. As used herein, a "transgenic animal" means a non-human animal, preferably a mammal, more preferably a rodent such as a rat or mouse, in which one or more of the cells of the animal includes a transgene. Other examples of transgenic animals include non-human primates, sheep, dogs, cows, goats, chickens, zebrafish, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse or a rat, in which an endogenous cis-acting KIM-1 regulatory sequences has been altered by homologous recombination between the endogenous gene and an exogenous DNA molecule introduced into a cell of the animal, e.g., an embryonic cell of the animal, prior to development of the animal.

A transgenic animal of the invention can be created by introducing cis-acting KIM-1 regulatory sequences into the male pronuclei of a fertilized oocyte, e.g., by microinjection, retroviral infection, or the like, and allowing the oocyte to develop in a pseudopregnant female foster animal. For example, a cis-acting KIM-1 regulatory sequence having the nucleic acid sequence of SEQ ID NO:3, or a functional fragment thereof, can be introduced as a transgene into the genome of a non-human animal. Alternatively, a nonhuman homologue of the human cis-acting KIM-1 regulatory sequences, such as a cis-acting KIM-1 regulatory sequence, can be isolated based on hybridization to the human cis-acting KIM-1 regulatory sequences (described further above) and used as a transgene. Intronic sequences and polyadenylation signals can also be included in the transgene to increase the efficiency of expression of the transgene. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, MANIPULATING THE MOUSE EMBRYO, Cold Spring Harbor Laboratory Press, Cold Spring Harbor, N.Y. (1996). Similar methods are used for production of other transgenic animals. A transgenic founder animal can be identified based upon the presence of the transgenic cis-acting KIM-1 derived regulatory sequences in its genome and/or expression of sequences operably linked to the transgenic cis-acting KIM-1 derived regulatory sequences. A transgenic founder animal can then be used to breed additional animals carrying the transgene. Moreover, transgenic animals carrying a transgene carrying a transgenic cis-acting KIM-1 derived regulatory sequence can further be bred to other transgenic animals carrying other transgenes.

To create a homologous recombinant animal, a vector is prepared which contains at least a portion of a cis-acting KIM-1 regulatory sequences gene into which a deletion, addition or substitution has been introduced to thereby alter, e.g., functionally disrupt, the cis-acting KIM-1 regulatory sequences. The cis-acting KIM-1 regulatory sequence can be a human sequence (e.g., SEQ ID NO:3), but more preferably, is a non-human homologue of a human cis-acting KIM-1 regulatory sequence. For example, a mouse homologue of human cis-acting KIM-1 regulatory sequence of SEQ ID NO:3 can be used to construct a homologous recombination vector suitable for altering a cis-acting KIM-1 regulatory sequence in the mouse genome.

In one embodiment, the vector is designed such that, upon homologous recombination, the endogenous cis-acting KIM-1 regulatory sequence is functionally disrupted (i.e., no longer encodes a functional protein; also referred to as a "knock out" vector).

Alternatively, the vector can be designed such that, upon homologous recombination, the endogenous cis-acting KIM-1 regulatory sequence is mutated or otherwise altered but is still functional (e.g., the upstream regulatory region can be altered to thereby alter the expression of the endogenous cis-acting KIM-1 regulatory sequence). In the homologous recombination vector, the altered portion of the cis-acting KIM-1 regulatory sequence is flanked at its 5' and 3' ends by additional nucleic acid of the cis-acting KIM-1 regulatory sequence to allow for homologous recombination to occur between the exogenous cis-acting KIM-1 regulatory sequence carried by the vector and an endogenous cis-acting KIM-1 regulatory sequence in an embryonic stem cell. The additional flanking cis-acting KIM-1 regulatory sequence is of sufficient length for successful homologous recombination with the endogenous gene. Typically, several kilobases of flanking DNA (both at the 5' and 3' ends) are included in the vector. See e.g., Thomas el al. (1987) Cell 51:503 for a description of homologous recombination vectors. The vector is introduced into an embryonic stem cell line (e.g., by electroporation) and cells in which the introduced cis-acting KIM-1 regulatory sequence has homologously recombined with the endogenous cis-acting KIM-1 regulatory sequence are selected (see e.g., Li et al. (1992) Cell 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Curr Opin Biotechnol 2:823–829; PCT International Publication Nos.: WO 90/11354; WO 91/01140; WO 92/0968; and WO 93/04169.

In another embodiment, transgenic non-human animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) PNAS 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

Identifying Trans-acting Factors that Bind to Cis-acting KIM-1-derived Regulatory Sequences Also provided are methods of identifying compounds that bind to cis-acting KIM-1-derived regulatory sequences. These compounds include trains-acting factors can include, e.g., polypeptides such as transcription factors, which interact preferentially with cis-acting KIM-1 regulatory sequences, or small molecules.

In one embodiment, a compound is identified by performing assays in which a cis-acting KIM-1 nucleic acid sequence is incubated with a test compound. Binding of the compound to the nucleic acid is detected using methods known in the art for assessing nucleic acid binding. For example, binding can be measured using electrophoretic mobility shift assays (EMSA). One way in which an EMSA can be prepared is to incubate together a DNA, which is preferably labeled, containing a KIM-1-derived cis-acting regulatory sequence and the test compound. The mixture is then subjected to electrophoresis, and the migration of the labeled nucleic acid in the presence of the test compound is compared to the migration of the labeled nucleic acid in the absence of the test compound. A difference in mobility indicates that the test compound binds to regulatory sequence.

Any suitable compound can be used as the test compound. In some embodiments, the test compound is obtained from a cellular extract known to contain, or to be suspected of containing, a trans-acting factor. Suitable cells include kidney cells, e.g., Cos cells.

Cell-based methods can also be used to identify compounds that modulate activity. For example, a cell containing a cis-acting KIM-1-derived regulatory sequence operably linked to a nucleic acid encoding a reporter molecule is contacted with a test compound and the reporter molecule mRNA or translated product is measured. mRNA levels and protein levels can be determined using any method known in the art, e.g. using Northern blot hybridization analysis, immunoprecipitations, or immunohistochemistry.

The trans-acting factors can also be identified using in vivo assays. For example, a reporter construct can be constructed in which a reporter gene is under the control of any of the cis-acting KIM-1-derived regulatory sequences disclosed herein.

The reporter gene can be any gene encoding a suitably detectable protein. The reporter gene can be, e.g., a gene encoding luciferase. Cells are transfected with the reporter construct that includes a cis-acting KIM-1 regulatory element. Transfection can be transient or stable. The cells can be transfected with more than one reporter construct. The transfected cells can then be incubated in the presence or absence of a test compound for an appropriate amount of time and the level of expression of the reporter gene is determined.

Similar assays can also be performed using a cell or nuclear extract instead of cells. Thus, in one embodiment, the invention provides a method for identifying a compound which modulates KIM activity. The method includes incubating a reporter construct that includes any of the regulatory elements according to the invention with a nuclear or cellular extract, or isolated nuclei, in the presence or absence of test compound. Expression of the test compound is then measured, e.g., by including a labeled nucleotide in the reaction and measuring the amount of label incorporated in the product transcribed from the reporter construct. Other methods can also be used to determine the amount of reporter gene expression in this system, such as the measure of the amount of protein expressed by the reporter gene.

In yet another embodiment, compounds that modulate the regulatory elements of the present invention in vivo can be identified in non-human animals. In one embodiment of the invention, a non-human animal, e.g., a mouse, is treated with a compound, such as a compound identified in one of the assays described above. After an appropriate amount of time, the level of activity is determined and compared to its activity in a mouse that has not received the test compound.

Pharmaceutical Compositions Containing Cis-acting KIM-1 Regulatory Sequences

Pharmaceutical compositions containing cis-acting KIM-1 regulatory sequences can be formulated in a conventional manner using one or more physiologically acceptable carriers or excipients.

Administration can be parenteral, intravenous, subcutaneous, intramuscular, retroperitoneal, intracranial, intraorbital, ophthalmic, intraventricular, intracapsular, intraspinal, intracisternal, intraperitoneal, transmucosal, or oral. The Nucleic acids can be provided in compositions formulated in various ways, according to the corresponding route of administration. For example, liquid solutions can be made for ingestion or injection. Gels or powders can be made for ingestion, inhalation, or topical application. Methods for making such formulations are well known and can be found in standard references in the field, for example, REMINGTON'S PHARMACEUTICAL SCIENCES, Mack Publishing Company, Easter, Pa., 15th Edition (1975).

The compositions can also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions can be presented in a pack or dispenser device that may contain one or more unit dosage forms containing the active ingredient. The pack may for example comprise metal or plastic foil, such as a blister pack. The pack or dispenser device may be accompanied by instructions for administration.

The therapeutic compositions can also contain a carrier or excipient. Useful excipients include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol.

Methods for Using Cis-acting KIM-1 Regulatory Sequences

Cells containing cis-acting KIM-1 regulatory sequences operably linked to a polypeptide-encoding sequence can be used to direct expression of the polypeptide. For example, the polypeptide can be expressed by providing a cell containing a KIM-1 regulatory sequence and culturing the cell, if necessary, to allow for expression of the polypeptide. Any cell type can be used as long as it allows for expression of the polypeptide-encoding sequence operably linked to the cis-acting regulatory sequence. In preferred embodiments, the cell is a renal cell.

In some embodiments, the expressed polypeptide is isolated. If desired, the polypeptide-encoding sequence can include a sequence encoding a signal sequence to allow for secretion of the polypeptide. The polypeptide can then be isolated from the extracellular medium.

The cis-acting KIM-1 regulatory sequences can also be used to increase transcription of an operably linked sequence in vitro or in vivo, e.g., in a cell, tissue or subject (such as a human). The operably linked sequence can be, e.g., a polypeptide-encoding sequence or an antisense nucleic acid construct. To increase transcription, a cell containing a cis-acting KIM-1 regulatory sequence operably linked to the sequence of interest, or a tissue containing two or more of such cells, is cultured under conditions that allow for the expression of the operably linked sequence to allow for increased levels of transcripts corresponding to the operably linked sequence in the cell or tissue. "Culture" as used herein can include in vitro culture under conditions necessary for maintaining the viability of mammalian cells, or in situ culture of cells in the body of an animal.

In another embodiment, the cis-acting KIM-1 regulatory sequences are used to direct expression of a nucleic acid sequence that is not normally under the control of such regulatory sequences. A nucleic acid molecule containing a cis-acting KIM-1 regulatory sequence is integrated into the genome of a target cell in the vicinity of a gene of interest. The gene of interest is preferably one that is normally not expressed in renal tissue, or is expressed at low amounts in renal tissue. Integration of the introduced cis-acting KIM-1 regulatory sequence near the gene of interest allows for the expression of the gene of interest under the control of the KIM-1 regulatory sequence. Preferably, the cis-acting KIM-1 regulatory sequences are introduced near the 5' region of the gene of interest.

Another use of the cis-acting KIM-1 regulatory sequences is to deliver a therapeutic polypeptide to renal tissue of a subject. To deliver the polypeptide, a cell including a cis-acting KIM-1 regulatory sequence operably linked to a therapeutic polypeptide-nucleic acid sequence is introduced into renal tissue. The sequences are expressed, e.g., by culturing the cell under conditions that allow for the expression of the linked polypeptide, to result in the delivery of the therapeutic polypeptide to the subject's renal tissue. In some embodiments, the therapeutic polypeptide linked to the cis-acting KIM-1 regulatory sequence is expressed following a stimulus. The stimulus can be, e.g., an injury such as ischemic injury or is ischemic reperfusion injury, or some other nephrotoxic injury.

The cis-acting KIM-1 regulatory sequences can also be used in a method for treating or preventing renal tissue injury in a subject. The method can include providing a cell in the subject that includes an introduced cis-acting KIM-1 regulatory sequence operably linked to a nucleic acid encoding a therapeutic nucleic acid, e.g., a therapeutic polypeptide-encoding sequence. The nucleic acid is allowed to express, and the gene product thereby introduced to the renal tissue to prevent or treat renal tissue injury in the subject. The cis-acting KIM-1 regulatory sequence can be introduced into the subject using methods described in the art for introducing nucleic acid sequences into cells. The nucleic acids can be introduced ex vivo or in vivo.

For gene therapy or antisense therapy, the claimed DNA may be introduced into target cells of an animal, e.g., a patient, using standard vectors and/or gene delivery systems. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy or antisense therapy may also be accomplished using a biolistic delivery system, such as that described by Williams et al., 1991, *Proc. Natl. Acad. Sci. U.S.A.* 88:2726–2729. Standard methods for transfecting cells with isolated DNA are well known to those skilled in the art of molecular biology. Gene therapy and antisense therapy to prevent or decrease the development kidney disease or injury may be carried out by directly administering the claimed DNA to a patient or by transfecting renal cells with the claimed DNA ex vivo and infusing the transfected cells into the patient.

A therapeutically effective amount is an amount of the DNA of the invention that is capable of producing a medically desirable result in a treated animal. As is well known in the medical arts, dosages for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{22}$ copies of the DNA molecule.

Nucleic acids can be delivered to a subject by any of a number of routes, e.g., as described in U.S. Pat. Nos. 5,399,346 and 5,580,859. Delivery can thus also include, e.g., intravenous injection, local administration, and systemic administration (see U.S. Pat. No. 5,328,470) or stereotactic injection (see e.g., Chen et al. (1994) *PNAS* 91:3054–3057).

The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

EXAMPLES

The following examples illustrate particular non-limiting embodiments of the invention.

Example 1

Cloning and Characterization of KIM-1 Derived Sequences

Cis-acting KIM-1 derived regulatory sequences were identified by screening a human genomic library with a 220 bp Not1-Kpn1 DNA fragment containing sequences in the 5' region of the human KIM-1 cDNA. The human KIM-1 cDNA is described generally in PCT publication WO97/44460 and Ichimura et al., *J. Biol. Chem.* 273:4135–42, 1998.

The screening identified a genomic fragment of 8933 bp (SEQ ID NO:1). The sequence of the 8933 bp region is shown in FIGS. 1A–1H. A translational start codon is present beginning at nucleotide 8655.

A 4817 bp KpnI-KpnI fragment (SEQ ID NO:2), which corresponds to nucleotides 3796–8612 of FIGS. 1A–1H, was subcloned into a luciferase-encoding pGL3b expression vector (Promega Corp.) and named p4.8KIM/pGL3b. The p4.8KIM/pGL3K construct is shown schematically in FIG. 2B. The presence of the 4817 bp KpnI-KpnI fragment in the pLUC3 was found to increase levels of encoded luciferase in renal cells, as is explained in more detail in the Examples, below.

A smaller sequence able to increase expression of luciferase in kidney cells was identified by subcloning a 1289 bp EcoR1-KpnI fragment (SEQ ID NO:3) corresponding to nucleotides 7322–8612 in FIG. 1 into a pLUC3 vector. The resulting construct was named 1.3 pKIM-1, and is shown schematically in FIG. 2C.

A construct named 0.5 pKIM, a pLUC3-based construct including only nucleotides 8110 to 8612 (SEQ ID NO:4) of FIG. 1, did not increase levels of luciferase as compared to expression. However, even though the region 8110 to 8612 is inactive alone, sequences present within the region may nevertheless be required, along with other sequences, to confer renal cell expression of linked sequences.

Example 2

Expression in Kidney Cells of Reporter Sequences Operably Linked to KIM-1 Derived Sequences Human genomic sequences from the 5' region of the human KIM-1 gene were tested for their ability to direct expression of a reporter polypeptide in three kidney-derived cell lines COS cells, a cell line derived from African green monkey kidney fibroblasts; LC/PK cells, a cell line derived porcine kidney epithelial cell lines; and MDCK cells, a cell line derived from canine kidney epithelial cells.

The cell lines were transiently transfected with constructs containing various regions of DNA from the human KIM-1 gene linked to a reporter luciferase gene. These constructs were concomitantly transfected with pCMV driven β-galactosidase vectors to standardize transfection efficiency, and activity of luciferase and β-galactosidase was measured. Activities were calculated as luciferase/β-gal ratios. Relative activities were calculated as the ratio of construct activity to negative control, i.e., promoterless luciferase vector (pGL3b).

DEAE-mediated transfection was used to introduce constructs (described in more detail below) into cell lines. Transfection was performed at 80% confluence, about 24 hours after seeding cells.

DNA was introduced into the cells by aspirating medium from the cells and mixing 10 ml of the appropriate culture medium (including 10% Nu serum, Collaborative Biomedical Products, #51004), 400 μl of DEAE (1×PBS+10 mg/ml DEAE Dextran+2.5 mM Chloroquine), and 20 μg of DNA (10 μg luciferase construct, 2 μg/β-gal vector, 8 μg BlueScript Vector).

Cells were exposed to DNA for 2–4 hours, after which the DNA solution was removed by aspiration and replaced with 5 ml 10% DMSO in 1×PBS. After 2 minutes, this solution was removed and the cells were washed twice with 1×PBS. Fresh medium was added, and cells were harvested after 48 hours.

Cells were washed once with 1×PBS, then incubated with 500 μl of 1×PBS. Cells were collected and centrifuged for 2 minutes, after which the supernatant was removed. Cells were resuspended in 200 μl of 0.25M TRIS, pH 7.8, and subjected to 3 shock freeze-thaw cycles, then centrifuged for 5 minutes at 14,000 g. The supernatant was used for luciferase and β Galactosidase assays.

To measure β-galactosidase activity, 25 µl of supernatant, 30 µl of 10×Mg buffer (90 mM $MgCl_2$, 1.02M beta-mercaptoethanol), 60 µl of 40 mM CPRG, and 48 µl of 0.5 sodium phosphate pH 7.5 were mixed and incubated until a red color developed. 500 µl of 1M $Na_2CO_3$ was added, and the OD at 570 nm was measured.

To measure luciferase activity 25 µl (p10) of the supernatant were mixed with 50 µl of 2× assay buffer, as per the manufacturer's instructions (Catalog # E 1502, Promega Corporation, Madison, Wis.). Measurements were made using a photoluminometer.

Figure 2B:
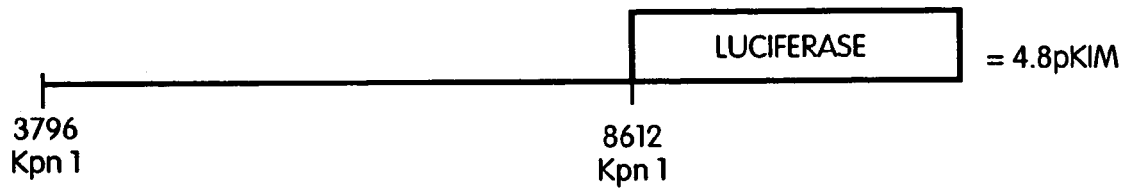
Figure 2C:
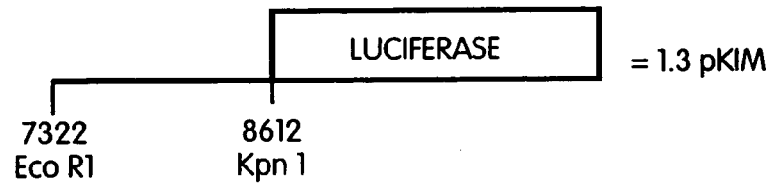
Figure 2D:
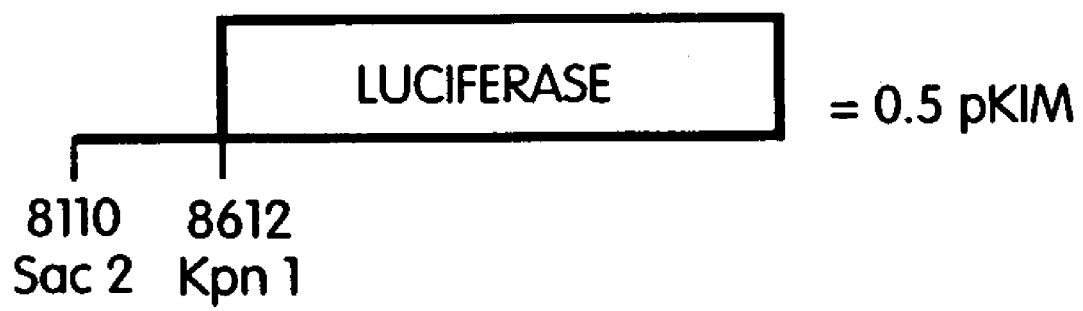

The KIM-1 human genomic region used to generate the constructs is shown in FIG. 2A. Constructs used in the transfection assays are shown in FIGS. 2B–2D. An 8933 bp fragment (SEQ ID NO:1) is shown schematically in FIG. 2A in a 5' to 3' orientation. KpnI sites are located at positions 3796 and 8612 as shown in the figure. For reference, the ATG initiation codon of the human KIM-1 occurs at position 8655.

The tested sequences are shown schematically in FIGS. 2B–2D. One tested sequence included a 4816 bp KpnI-KpnI fragment from the 5' flanking region of the human KIM-1 gene. This fragment corresponds to the sequences bordered by KpnI sites at positions 3796 and 8612 of MZ007. FIG. 2B illustrates a construct made by inserting the 4816 bp KpnI-KpnI fragment into a pLUC3 Basic expression vector (Promega Corporation). The resulting construct was named 4.8 pKIM/PGL3b.

A shorter fragment from the 4816 bp KpnI-KpnI region was also tested. This fragment was defined by an EcoRI-KpnI fragment encompassing nucleotides 7322–8611 of MZ007. This KpnI fragment was inserted into the pLUC3 Basic expression vector and named 1.3 pKIM/pGL3b. This construct is shown schematically in FIG. 2C.

A still shorter fragment defined by a SacII-KpnI fragment encompassing nucleotides 8110–8612 of MZ007 was also examined. This construct was named 0.5 pKIM/pGL3b and is shown schematically in FIG. 2D.

For each cell line tested, relative luciferase activities were calculated by measuring luciferase following transfection with no plasmid (i.e., zero, "0"), the pGL3 Basic vector alone ("pGL3"), or the constructs 4.8 pKIM/pGL3b, 1.3 pKIM/pGL3b, and 0.5 pKIM/pGL3b.

Figure 3:
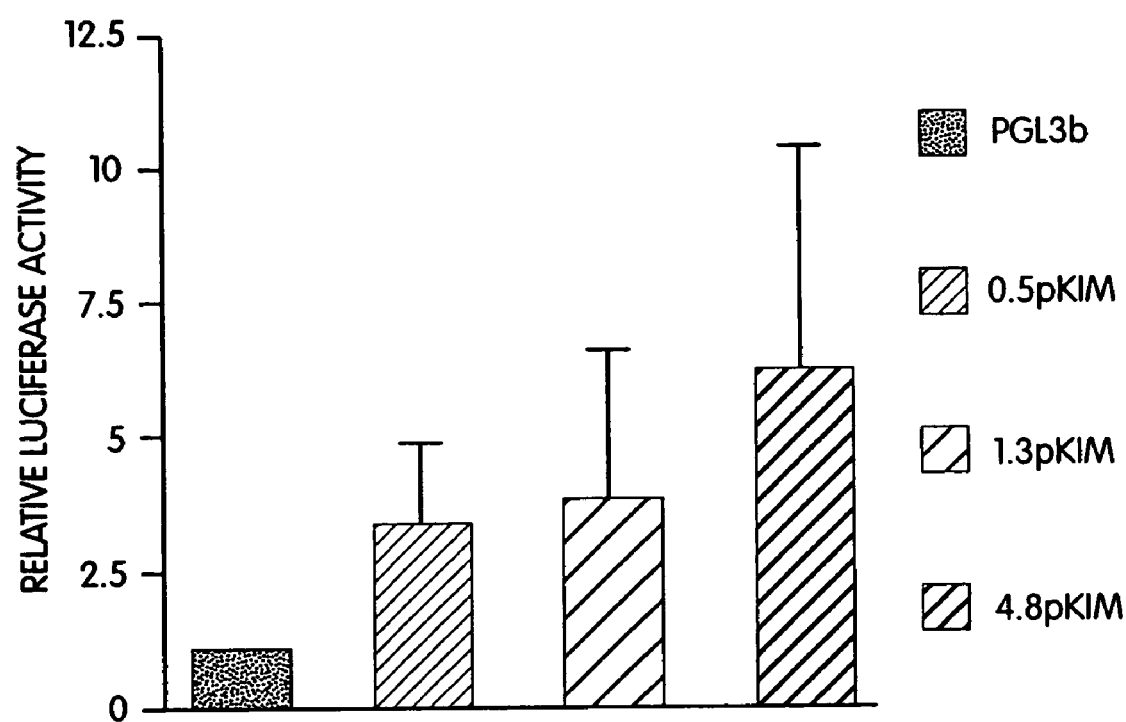
FIG. 3 is a bar graph showing relative expression of luciferase in COS monkey kidney cells of various reporter constructs containing sequences from the 5' region of the human KIM-1 gene

For transformations into COS cells, DMEM was used as the culture medium. For the 4.8 pKIM construct, four trials were performed, each using 2 plates. The RA was 3.8, with SD of 2.82. For the 1.3 pKIM construct, four trials were performed, each using 2 plates. The RA was 6.3, with an SD of 4.19. For the 0.5 pKIM construct, 2 trials were performed, each using 2 plates. The RA as 3.3, with an SD of 1.54. The results of the transfection assays using the COS cells are shown in FIG. 3.

Figure 4:
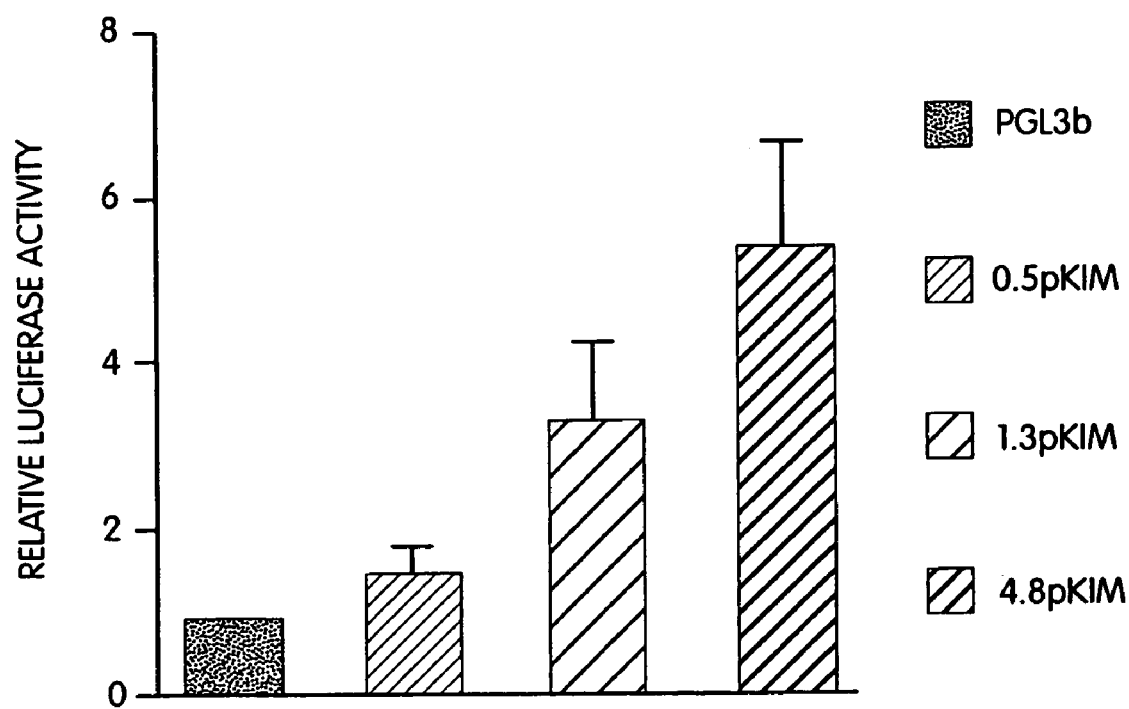
FIG. 4 is a bar graph showing relative expression of luciferase in LLCPK cells of various reporter constructs containing sequences from the 5' region of the human KIM-1 gene.

For transformations into LLC-PK cells, DMEM was used as the culture medium. For the 4.8 pKIM/PGL3b construct, three trials were performed, each using 2 plates. The RA was 5.5, with a SD of 1.43. For the 1.3 pKIM/PGL3b construct, three trials were performed, each using 2 plates. The RA was 3.4, with an SD of 0.89. For the 0.5 pKIM/PGL3b construct, two trials were performed, using 2 plates each. The RA was 1.5, with an SD of 0.34. The results of the transfection assays using LLC-PK cells are summarized in FIG. 4.

Figure 5:
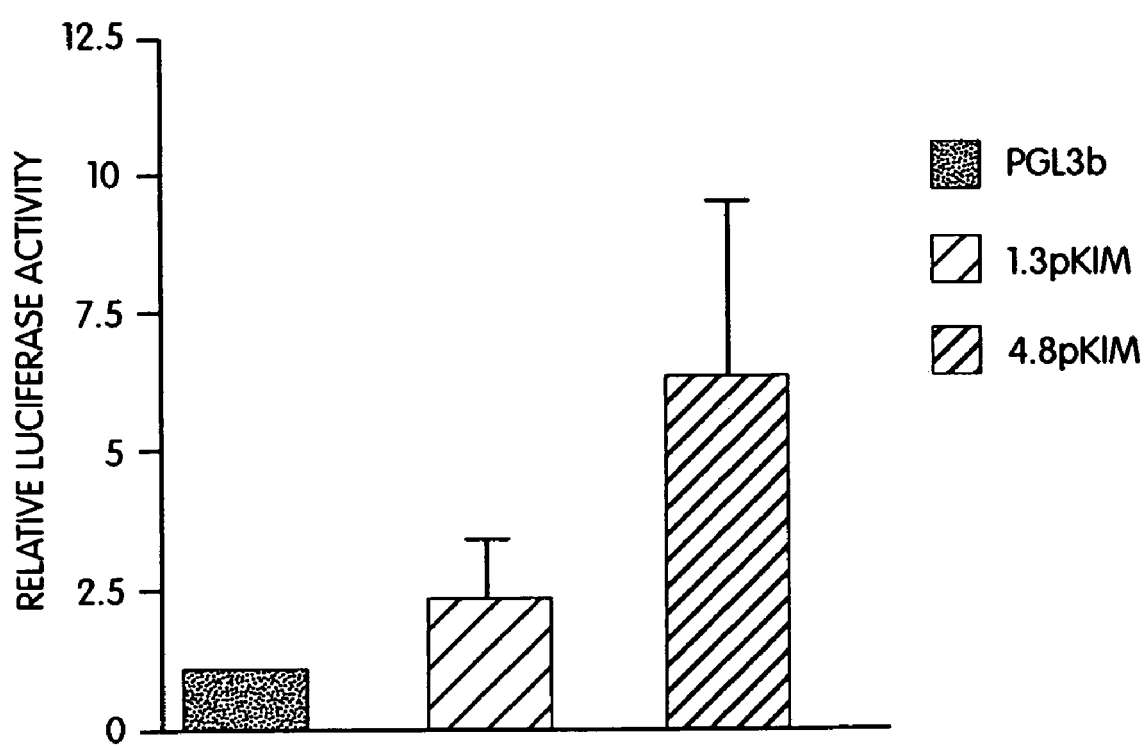
FIG. 5 is a bar graph showing relative expression of luciferase in MDCK cells of various reporter constructs containing sequences from the 5' region of the human KIM-1 gene.

For transformations into MDCK cells, MEM was used as the culture medium. For the 4.8 pKIM construct, 3 trials were performed, using 2 plates each. The relative activity (RA) was 7.0, and the SD was 3.46. For the 1.3 pKIM/PGL3b construct, 3 trials were performed, each using 2 plates. The relative activity was 3.4, with a SD of 0.89. The results for the transfection assays using MDCK cells are shown in FIG. 5.

In assays using COS cells (FIG. 3), LLC/PK1 cells (FIG. 4), and MDCK cells (FIG. 5), luciferase activity was significantly higher in cells transfected with the constructs 4.8 pKIM/pGL3b and 1.3 pKIM/pGL3b as compared to cells transfected with pGL3 alone, and cells not transfected with any construct.

Figure 6:
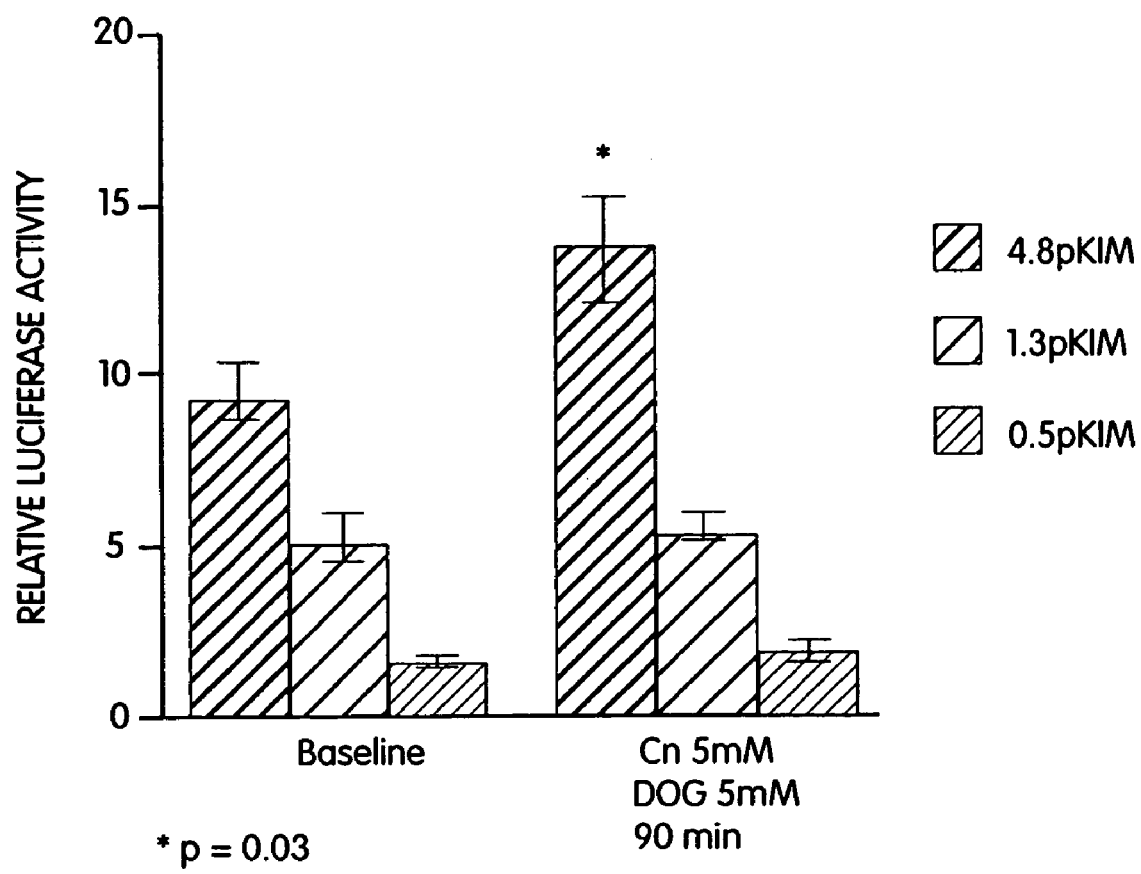
FIG. 6 is a bar graph showing inducibility of sequences linked to a KIM-1 regulatory sequence in HK2 cells after exposure to reactive oxygen species (ROS) or anoxia.
Figure 7:
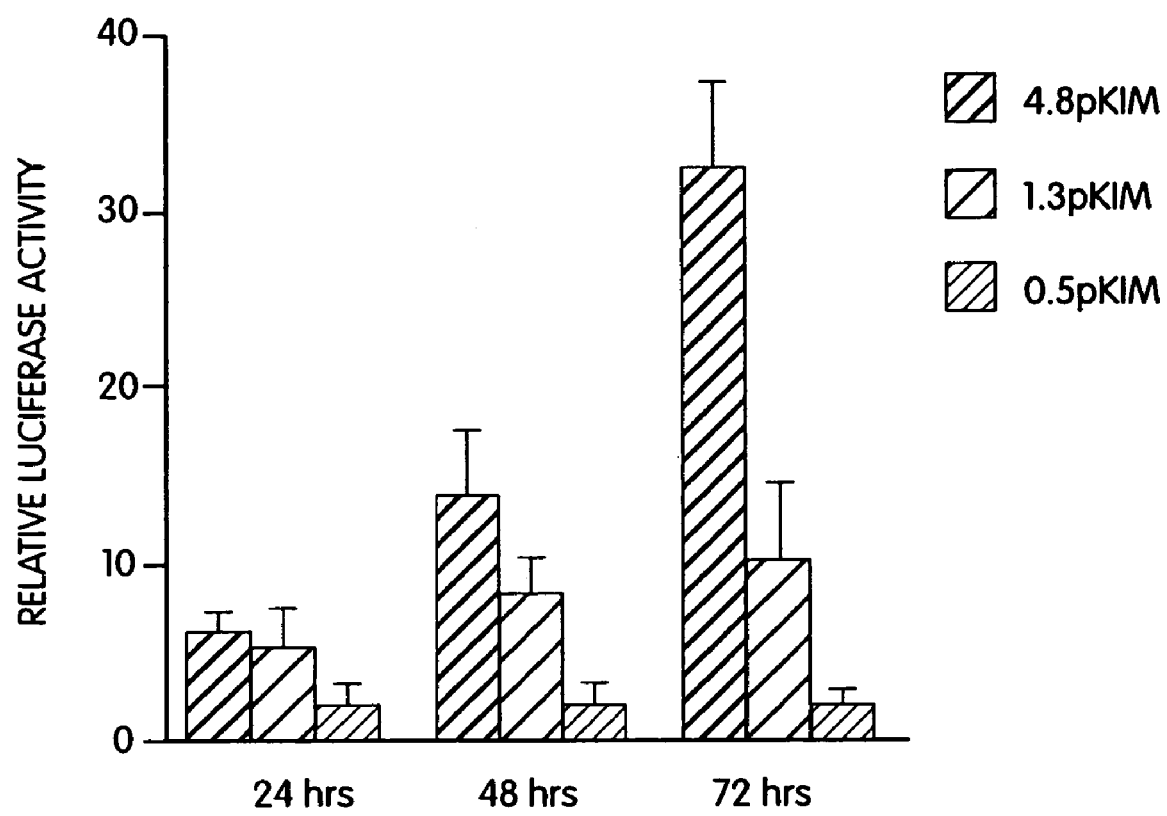
FIG. 7 is a bar graph showing relative expression of luciferase in MDCK cells at various timepoints after transfection with reporter constructs containing sequences from the 5' region of the human KIM-1 gene.

These results indicate that sequences nucleotides 7322–8612 as shown in FIGS. 1A–H contain cis-acting regulatory elements that are able to increase expression of operably liked sequences in kidney tissues. Additional elements that increase this activity may be in 3796–7322 region, as is shown in FIG. 6, as is discussed in Example 3, below.

The 0.5 pKIM/pGL3b construct did not increase expression of luciferase relative to cells transfected with pGL3 alone in the cell types tested. While these results suggest that these KIM-1 derived sequences did not confer expression of linked sequences, at least in the cell lines and conditions used, these results do not exclude the possibility that this region of the KIM-1 flanking region contains elements that are necessary or important for increasing expression of linked sequences in kidney tissues.

Example 3

Expression in Kidney Cells of Reporter Sequences Operably Linked to KIM-1 Derived Sequences Following Injury Expression of luciferase encoded by 4.8 pKIM, 1.3 pKIM, and 0.5 pKIM was measured in transfected HK2 cells that had been subjected to chemical anoxia using cyanide and deoxyglucose. HK2 cells are derived from epithelial proximal tubule cells from human kidney.

A 12-well plate system (MULTIWELL™ 12-well, Becton-Dickson) was used in these studies. The culture medium used was EGM (Clontech). Prior to transformation, 2 ml medium per well was added to the cells, then removed by aspiration. HK2 cells were seeded at a density of 30,000/well. Cells reached 80% confluence after 16–24 hours.

DNA was prepared by mixing 50 µl of serum free medium, 5 µg of DNA (2.5 µg luciferase construct, 0.5 µg β-galactosidase vector, 2 µg BlueScript vector), and 5 µl of SUPERFECT reagent (Qiagen Corp.), and incubating for 7 minutes. 300 µl of medium+10% FCS was added, and the mix was then added to the cells. The cells were then allowed to incubate for 2 hours. The DNA solution was next removed by aspiration, after which the cells were washed twice in 1×PBS, after which the cells were incubated in culture medium with 10% FCS.

To induce chemical anoxia, medium was removed by aspiration, and cells were washed once with 1×PBS. Cells were then incubated for 90 minutes in 1 ml Krebs-Henseleit buffer ("KHB") (6.72 mM NaCl, 3.6 mM KCl, 1.3 mM KH2PO4, 25 mM $NaHCO_3$, 1 mM $CaCl_2$, a mM $MgCl_2$, ph7.4 in incubator), along with 5 mM sodium cyanide and 5 mM deoxyglucose. Cells were then washed once with 1×PBS and incubated in KHB+10 mM dextrose for 15–20 minutes, then harvested as explained below.

For harvesting, cells were washed once in 1×PBS, then incubated for 5 minutes with 200 µl 25 mM GlyGly, 15 mM MgSO4, 4 mM EGTA, pH 8.0, 1% Triton X 100, 1 mM DTT. Lysate was then removed from the wells and used for luciferase and β galactosidase assays.

To assay for β galactosidase activity, 50 μl of cell extract was mixed with 50 μl of assay buffer (Catalog # E2000, Promega Corporation, Madison, Wis.), followed by incubation at 37° C. until a faint yellow color developed. Signals were then measured in an ELISA reader at 405 nm.

Luciferase activity was measured by mixing 50 μl of 2× assay buffer as indicated by the manufacturer (Catalog #E1502, Promega, Madison, Wis.). Measurements were made using a photoluminometer.

Luciferase expression was measured in three different populations of transfected HK2 cells. The first group included cells not subjected to chemical anoxia. These cells were assayed 72 hours following transfection. The second group included cells assayed 72 hours following transfection and 90 minutes after inducement of chemical anoxia. For each group of cells, separate populations of cells were transfected with 4.8 pKIM/pGL3b, 1.3 pKIM/GL3b, and 0.5 pKIM/pGL3b.

The results are illustrated in FIG. 6. For baseline cells, the 4.8 pKIM/pGL3b construct yielded a RA of 9.1, with a SEM of 1.1. The 1.3 pKIM/pGL3b construct yielded a RA of 5.0, with a SEM of 0.8. The 0.5 pKIM constructed yielded a RA of 1.6, with a SEM of 0.2.

In cells subjected to chemical anoxia, the 4.8 pKIM/pGL3b generated a RA of 13.5, with a SEM of 1.5. The 1.3 pKIM/pGL3b construct yielded a RA of 5.6, with a SEM of 0.4. The 0.5 pKIM/pGL3b construct generated a RA of 2.0, with a SEM of 0.3.

These data demonstrate that KIM-1 sequences present in the 4.8 pKIM/pGL3b construct caused higher levels of expression of the linked luciferase gene in cells subjected to anoxia, as compared to control cells. This effect was not seen with the 1.3 pKIM/pGL3b and 0.5 pKIM/pGl3b constructs in this experiment.

Example 4

Expression in Confluent Kidney Cells of Reporter Sequences Operably Linked to KIM-1 Derived Sequences Expression of a luciferase gene linked to 4.8 pKIM/PGL3b, 1.3 pKIM/PGL3b, or 0.5 pKIM/PGL3b in confluent cells was investigated.

MDCK cells were transfected with the indicated construct 16–24 hours after seeding. Transfected cells were harvested after 24, 48, and 72 hours, and luciferase and β-galactosidase activity was then measured. The results are summarized below:

TABLE 1

|  | RA | SD |
| --- | --- | --- |
| 24 hours, 80% confluence | | |
| 4.8 pKIM/PGL3b | 5.65 | 0.97 |
| 1.3 pKIM/PGL3b | 4.93 | 2.07 |
| 0.5 pKIM/PGL3b | 2.03 | .98 |
| 48 hours, 90% confluence | | |
| 4.8 pKIM/PGL3b | 13.55 | 3.5 |
| 1.3 pKIM/PGL3b | 7.95 | 1.91 |
| 0.5 pKIM/PGL3b | 2.4 | .61 |
| 72 hours, 100% confluence | | |
| 4.8 pKIM/PGL3b | 31.8 | 6.5 |
| 1.3 pKIM/PGL3b | 9.83 | 4.82 |
| 0.5 pKIM/PGL3b | 1.93 | 1.09 |

These results demonstrated that KIM-1 sequences present in 4.8 pKIM/pGL3B lead to significantly higher levels of luciferase as cells reach confluency. KIM-1 sequences present only in the 1.3 pKIM/pGL3B and 0.5 pKIM/pGL3B constructs did not increase expression of luciferase in these studies.

Example 5

Use of KIM-1-derived Cis-acting Regulatory Sequences in Gene Therapy

KIM-1 derived cis-acting regulatory sequences according to the invention can be used for gene therapy treatment of renal diseases. KIM-1 cis-acting regulatory sequences can be used alone or as part of a vector to express heterologous genes, e.g., a KIM-1 cDNA, or a protein other than a KIM-1 polypeptide, in renal cells.

The DNA or vector containing a KIM-1 cis-acting regulatory sequence linked to a nucleic acid encoding a polypeptide of interest is introduced into renal cells, which in turn produce the polypeptide of interest. For example, sequences encoding the desired polypeptide may be operably linked to the renal cell-specific promoter sequences of the invention and expressed in renal cells.

Example 6

Use of KIM-1-derived Cis-acting Regulatory Sequences in Antisense Therapy

The KIM-1 cis-acting regulatory sequence is used in methods of antisense therapy. Antisense therapy is carried out by administering to an animal, e.g., a human patient, DNA containing the renal cell-specific promoter sequences of the invention operably linked to a DNA sequence, i.e., an antisense template, which is transcribed into an antisense RNA. The antisense RNA is a short nucleotide sequence (generally at least 10 nucleotides, preferably at least 14 nucleotides, and up to 100 or more nucleotides) formulated to be complementary to a portion of a specific mRNA sequence. The antisense template is preferably located downstream from the promoter sequences of the invention. A poly A tail element is typically located at the end of the antisense sequence to signal the end of the sequence. Standard methods relating to antisense technology have been described. See, e.g., Melani et al., *Cancer Res.* 51:2897–2901, 1991. Following transcription of the DNA sequence into antisense RNA, the antisense RNA binds to its target mRNA molecules within a cell, thereby inhibiting translation of the mRNA and down-regulating expression of the protein encoded by the mRNA.

The expression of other renal cell proteins may also be inhibited in a similar manner. For example, the DNA of the invention can be operably linked to antisense templates that are transcribed into antisense RNA capable of inhibiting the expression of the following proteins: TGF-β, dysfunctional collagen mutant genes, WT-1 (Wilms Tumor gene), and genes associated with polycystic kidney disease (PCK).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated DNA comprising the nucleotide sequence of SEQ ID NO:3.
2. The DNA of claim 1, wherein said DNA comprises SEQ ID NO:2.
3. A vector comprising the DNA of claim 1.
4. An isolated cell comprising the vector of claim 3.
5. The DNA of claim 1, wherein said DNA is operably linked to a sequence encoding a KIM-1 antisense nucleic acid.
6. The DNA of claim 1, wherein the DNA is operably linked to at least one polypeptide-encoding sequence.
7. The DNA of claim 6, wherein said polypeptide-encoding sequence encodes a KIM-1 polypeptide.
8. The DNA of claim 7, wherein said KIM-1 polypeptide comprises the amino acid sequence of a human KIM-1 polypeptide.
9. The DNA of claim 6, wherein said polypeptide-encoding sequence does not encode a KIM-1 polypeptide.
10. The DNA of claim 6, wherein said polypeptide-encoding sequence encodes a therapeutic polypeptide.
11. The DNA of claim 6, wherein said polypeptide is selected from the group consisting of a cell survival-promoting factor, a cell growth-promoting factor, a wound-healing factor, an anti-fibrotic factor, an apoptosis-inhibiting factor, an anti-inflammatory factor, a terminal differentiation-promoting factor, a cell growth-inhibiting factor, an intravascular-volume restoration factor, a chelating agent, an alkylating agent, an angiotensin-converting enzyme-inhibiting factor, erythropoietin, a cytokine, a receptor, an anticoagulant, an enzyme, a hormone, an antibody, and a renal structural protein.
12. The DNA of claim 6, wherein said polypeptide is selected from the group consisting of an insulin growth factor (IGF), an epidermal growth factor (EGF), a fibroblast growth factor (FGF), a transforming growth factor beta (TGF β) Type II receptor, a hepatocyte growth factor (HGF), and an endothelial cell adhesion molecule ICAM-1.
13. A method of directing expression of a recombinant polypeptide, said method comprising:
    a) providing a cell comprising the DNA of claim 6; and
    b) culturing said cell under conditions that allow for the expression of said polypeptide;
    thereby directing expression of said polypeptide.
14. The method of claim 13, wherein said cell is a renal cell.

* * * * *